(12) United States Patent
Martin et al.

(10) Patent No.: US 10,391,288 B2
(45) Date of Patent: Aug. 27, 2019

(54) IMPLANTABLE DEVICE FOR LONG-TERM DELIVERY OF DRUGS

(71) Applicant: Delpor, Inc., San Francisco, CA (US)

(72) Inventors: Francis J. Martin, San Francisco, CA (US); Ling-Ling Kang, Palo Alto, CA (US)

(73) Assignee: Delpor, Inc., Brisbane, CA (US)

( * ) Notice: Subject to any disclaimer, the term of this patent is extended or adjusted under 35 U.S.C. 154(b) by 366 days.

(21) Appl. No.: 15/388,298

(22) Filed: Dec. 22, 2016

(65) Prior Publication Data

US 2017/0100571 A1    Apr. 13, 2017

Related U.S. Application Data

(63) Continuation of application No. 12/918,369, filed as application No. PCT/US2010/027037 on Mar. 11, 2010, now Pat. No. 9,561,352.

(60) Provisional application No. 61/159,742, filed on Mar. 12, 2009.

(51) Int. Cl.
| | | |
|---|---|---|
| *A61M 31/00* | (2006.01) | |
| *A61K 9/00* | (2006.01) | |
| *A61K 31/505* | (2006.01) | |
| *A61K 47/34* | (2017.01) | |
| *A61K 31/407* | (2006.01) | |

(Continued)

(52) U.S. Cl.
CPC ......... *A61M 31/002* (2013.01); *A61K 9/0024* (2013.01); *A61K 9/0092* (2013.01); *A61K 31/407* (2013.01); *A61K 31/505* (2013.01); *A61K 31/519* (2013.01); *A61K 47/34* (2013.01); *A61M 37/00* (2013.01)

(58) Field of Classification Search
CPC ... A61M 31/002; A61M 37/00; A61K 9/0024; A61K 9/0092
See application file for complete search history.

(56) References Cited

U.S. PATENT DOCUMENTS

| | | |
|---|---|---|
| 3,896,819 A | 7/1975 | Zaffaroni et al. |
| 3,948,254 A | 4/1976 | Zaffaroni |
| 3,948,262 A | 4/1976 | Zaffaroni |

(Continued)

FOREIGN PATENT DOCUMENTS

| | | |
|---|---|---|
| WO | WO 2003/024357 A2 | 3/2003 |
| WO | WO 2007/011955 A2 | 1/2007 |

(Continued)

OTHER PUBLICATIONS

Amann, et al., "In Vitro-In Vivo Correlations of Scalable PLGA-Risperidone Implants for the Treatment of Schizophrenia," Pharm Res, vol. 27, pp. 1730-1737.

(Continued)

*Primary Examiner* — Matthew F Desanto
(74) *Attorney, Agent, or Firm* — McDermott Will & Emery LLP; Judy M. Mohr

(57) ABSTRACT

A device for sustained delivery of a poorly water soluble drug is described. A drug reservoir within the device, when in operation, contains an aqueous suspension of the drug mixed with a suspension of an excipient that, in one embodiment, generates acidic groups for a sustained period of time to maintain a desired pH in the aqueous suspension that in turn provides a constant concentration of a soluble form of the drug.

17 Claims, 7 Drawing Sheets

(51) Int. Cl.
*A61K 31/519* (2006.01)
*A61M 37/00* (2006.01)

(56) References Cited

U.S. PATENT DOCUMENTS

| | | | |
|---|---|---|---|
| 3,993,072 | A | 11/1976 | Zaffaroni |
| 3,993,073 | A | 11/1976 | Zaffaroni |
| 4,220,153 | A | 9/1980 | Dresback |
| 5,266,325 | A | 11/1993 | Kuzma et al. |
| 5,728,396 | A | 3/1998 | Peery et al. |
| 5,798,042 | A | 8/1998 | Chu et al. |
| 8,263,108 | B2 * | 9/2012 | Gibson ............... A61F 2/02 424/422 |
| 9,433,573 | B2 | 9/2016 | Martin et al. |
| 9,433,574 | B2 | 9/2016 | Martin et al. |
| 9,561,352 | B2 | 2/2017 | Martin et al. |
| 2002/0102307 | A1 * | 8/2002 | Guo ............... A61K 9/0051 424/473 |
| 2003/0064095 | A1 * | 4/2003 | Martin ............... A61K 9/0004 424/451 |
| 2004/0133154 | A1 | 7/2004 | Flaherty et al. |
| 2004/0172005 | A1 | 9/2004 | Arenberg et al. |
| 2005/0118229 | A1 * | 6/2005 | Boiarski ............... A61K 9/0024 424/424 |
| 2006/0116641 | A1 | 6/2006 | Gordon et al. |
| 2006/0153895 | A1 | 7/2006 | Siegel et al. |
| 2006/0159721 | A1 | 7/2006 | Siegel et al. |
| 2006/0246138 | A1 | 11/2006 | Rohloff et al. |
| 2007/0053963 | A1 | 3/2007 | Hotchkiss et al. |
| 2008/0131513 | A1 | 6/2008 | Woo et al. |
| 2008/0177153 | A1 | 7/2008 | Bachman et al. |
| 2008/0213331 | A1 | 9/2008 | Gelfand et al. |
| 2008/0305140 | A1 | 12/2008 | Siegel et al. |
| 2011/0106006 | A1 | 5/2011 | Martin et al. |
| 2015/0258017 | A1 | 9/2015 | Martin et al. |
| 2015/0258018 | A1 | 9/2015 | Martin et al. |

FOREIGN PATENT DOCUMENTS

| | | |
|---|---|---|
| WO | WO 2007/040938 A1 | 4/2007 |
| WO | WO 2010/105093 A2 | 9/2010 |

OTHER PUBLICATIONS

International Search Report from PCT Patent Application No. PCT/US2010/027037 dated Dec. 6, 2010, application now published as International Publication No. WO2010/105093 dated Sep. 16, 2010.

Rabin, et al., "In vitro and in vivo demonstration of risperidone implants in mice", Schizophr Res., vol. 98, No. 1-3, pp. 66-78 (2008).

\* cited by examiner

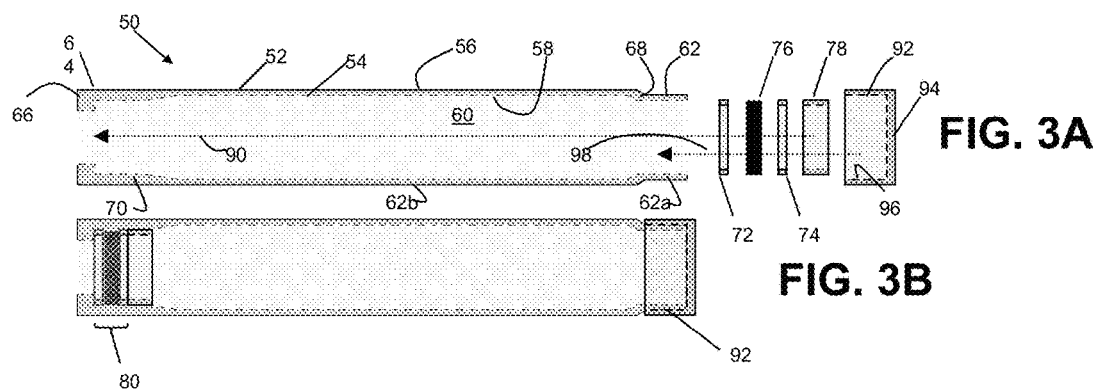
FIG. 3A
FIG. 3B
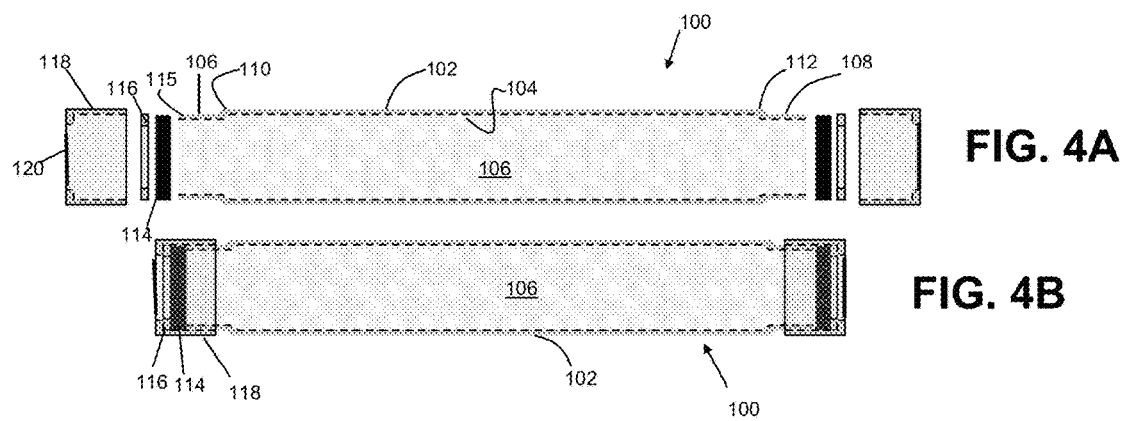
FIG. 4A
FIG. 4B

IMPLANTABLE DEVICE FOR LONG-TERM DELIVERY OF DRUGS

CROSS-REFERENCE TO RELATED APPLICATIONS

This application is a continuation of U.S. application Ser. No. 12/918,369, filed Dec. 17, 2010, now U.S. Pat. No. 9,561,352, which is a U.S. National Stage of International Patent Application No. PCT/US2010/027037, filed Mar. 11, 2010, which claims the benefit of U.S. Provisional Application No. 61/159,742, filed Mar. 12, 2009, each of which is incorporated herein by reference in its entirety.

TECHNICAL FIELD

The subject matter described herein relates to drug delivery, and in particular, to an implantable drug-delivery device designed for delivery of a therapeutic agent at a constant rate over an extended period.

BACKGROUND

For a variety of therapeutic agents, it would be desirable to deliver an active pharmaceutical ingredient (e.g., an agent or a drug) into the bloodstream from a subcutaneously implanted device in a subject at a substantially constant rate over a sustained period of up to several months. For selected drugs, this delivery pattern can provide substantial clinical benefits to patients and address important unmet medical needs.

In general, there are two challenges that must be overcome in implementing an effective, long-term drug-delivery device of this type. First, the amount of drug delivered by the implanted device must be sufficient to provide the desired therapeutic effect and be substantially constant over time; that is, the release profile approximates zero-order kinetics, so that the treated individual receives a substantially constant therapeutic dose over a specific time period without dose spiking or periods of sub-therapeutic delivery. Secondly, the device should be capable of holding an amount of drug sufficient for releasing a therapeutic dose of compound over an extended period, e.g., 1-6 months, with a size and shape suitable for implantation in a selected anatomical site. For example, a device intended to be implanted in a subcutaneous site preferably has an elongate shape and a cross-sectional depth of less than about 5-6 mm so as be accommodated in the limited depth of the subcutaneous space and not to produce an unsuitably large bulge in the skin above the implantation site. The device would preferably need to less than about 50 mm in overall length so that normal movement would not cause the device to erode the surrounding tissues, particularly at the ends of the device where, during normal movement, bending of the device relative to the plane of tissue may occur resulting in rupture of the device through the skin surface. Given these constrains, the maximum practical volume of the drug reservoir of a subcutaneously implanted device is generally considered to be in the range of 500 microliter (µL), assuming that substantially all of the volume enclosed by the device walls is available to serve as a drug reservoir.

A preferred shape for a subcutaneously implantable device is cylindrical. Cylindrical devices may be implanted by placing the device in an implanter tool or trocar, an open-ended, pointed cannula with an inner diameter slightly larger than the outer diameter of the device. The trocar, loaded with the device, is inserted, through a small incision, and tunneled under the skin distally from the entry point. The device is positioned by retracting the trocar shaft mechanically, or by removing the trocar while placing pressure on the end of the device using a rod or plunger passed through the opposite end of the trocar shaft, leaving the device in place under the skin.

The art describes implantable drug delivery devices. For example, implantable osmotic pumps are known (e.g., U.S. Pat. No. 5,728,396). These drug delivery pumps suffer from a lack of sufficient internal volume for extended delivery of low-water soluble drugs at a therapeutic rate because the osmotic engine occupies as much as 50% of the available internal volume. These drug delivery pumps are also prone to clogging of the exit port by precipitation of drug held in solution within the reservoir which can lead to rapid shut down, possible device rupture and/or dose dumping.

The foregoing examples of the related art and limitations related therewith are intended to be illustrative and not exclusive. Other limitations of the related art will become apparent to those of skill in the art upon a reading of the specification and a study of the drawings.

BRIEF SUMMARY

The following aspects and embodiments thereof described and illustrated below are meant to be exemplary and illustrative, not limiting in scope.

In one aspect, a drug delivery device is provided. The device comprises a non-erodible, non-porous housing member defining a reservoir, the housing member having first and second opposing ends. A porous partition is positioned in the first end of the housing member, and contained within the reservoir is a drug formulation comprised of a sparingly soluble drug and a solubility-modifying excipients. The solubility-modifying excipient is effective to provide a concentration of the drug, in an aqueous suspension when the drug formulation is hydrated, sufficient to provide release of a therapeutic dose of the drug from the device over a period of more than one month, as soluble drug diffuses out of the device across the partition.

In one embodiment, the housing member is water impermeable.

In another embodiment, the housing member is a metal.

In one embodiment, the porous partition is selected from a porous polymer membrane, a sintered metallic membrane, and a ceramic membrane.

In one embodiment, the solubility-modifying excipient is a biocompatible, bioerodible polymer. In an exemplary embodiment, the polymer is selected from polylactides, polyglycolides, copolymers thereof and polyethyleneglycol. In a preferred embodiment, the polymer is a co-polymer of polylactic acid and polyglycolic acid monomeric units, wherein the polylactic acid content is between about 50% to 100%.

In one embodiment, the drug is a neuroleptic agent. In exemplary embodiments, the neuroleptic agent is risperidone, 9-hydroxyrisperidone or a pharmaceutically acceptable salt thereof. In other embodiments, the neuroleptic agent is olanzapine, paliperidone, asenapine, haloperidol or aripiprazole or a pharmaceutically acceptable salt thereof.

In one embodiment, the total amount of neuroleptic agent loaded is the reservoir is greater than 100 mg.

In yet another embodiment, the drug is buprenorphine.

In still another embodiment, the drug is present in soluble and insoluble forms in a total amount of greater than 100 mg/mL.

In one embodiment, the soluble fraction of drug is less than 1% of the total.

In another aspect, a method for delivering a sparingly soluble drug from an aqueous suspension into an environment of use is provided. The method comprises formulating the drug with an excipient effective to maintain a substantially constant concentration of a soluble form of the drug in the aqueous suspension to sustain release of a therapeutic amount of the drug into an environment of use for at least 30 days.

In another aspect, a method of treating a patient is provided. The method comprises providing a device as described herein, and implanting the device in the patient. In one embodiment, the method is for treating a patient suffering from a psychotic disorder, wherein the drug is a neuroleptic agent and is delivered at a substantially constant release rate for between 1-6 months.

In one embodiment, the device is implanted subcutaneously.

In another aspect, an implantable device for use in releasing a therapeutic agent at an implantation site in a subject, at a substantially constant release rate over a selected time period between about 1-6 months is provided. The device comprises, in operative condition, an housing that defines an interior chamber, the housing formed of a non-erodible, non-porous material; a partition affixed to an end of the housing, the partition comprising a plurality of pores which allow therapeutic agent in a soluble form, but not in an insoluble form, to diffuse out of the chamber into an external medium, and contained within the chamber, in operative condition when the chamber is hydrated, an aqueous suspension composed of a mixture of a poorly water soluble therapeutic agent having a soluble agent form and an insoluble agent form and a solubility-modifying excipient. The solubility-modifying excipient acts to produce a concentration of the soluble agent form sufficient to provide a therapeutic dose of the drug over a selected time period, as the soluble agent form diffuses out of the device across the partition by means of a concentration gradient of soluble agent form in the chamber and in the environment of use.

In one embodiment, the device is cylindrical in shape, and its outer surface is devoid of pits, ridges or pores. One or both of the circular cylinder ends is fitted with the porous partition, and the overall outer surface area of the device is less than 7 cm$^2$.

In another aspect, an implantable device for use in releasing a therapeutic agent at an implantation site in a subject, at a substantially constant release rate over a selected time period between about 1-6 months, is provided. The device comprises an interior reservoir defined by a housing member, and contained within the reservoir a therapeutic agent. The device also comprises a partition separating the reservoir from an external medium, the partition containing multiple pores which allow therapeutic agent in soluble form, but not in insoluble form, to diffuse out of the reservoir into the external medium, the pores, in one embodiment, occupying less than 1.7 cm$^2$ of the total surface of the chamber. Contained within the reservoir, in operative condition when the reservoir is hydrated, is an aqueous suspension comprised of a mixture of the therapeutic agent and a solubility-modifying excipients. The therapeutic agent has a water solubility at neutral pH such that the concentration of the agent in the water phase of the suspension is insufficient to drive outward flux of a therapeutic dose of the agent. The excipients acts to produce a concentration of a soluble form of the agent sufficient to provide a therapeutic dose over the selected time period, as soluble agent diffuses out of the device across the partition by means of a concentration gradient of soluble agent across the partition.

In one embodiment, the pH of said suspension is adjusted to be in the range of 2.5 to 6.8 and to control the equilibrium water solubility of the agent.

In another embodiment, the solubility-modifying agent is a polymer mixture selected to erode at a rate that corresponds to the intended period of operation of said device. In one embodiment, the polymer is a polylactide, polyglycolide co-polymer particle of a particle size, molecular weight, acid end-group concentration, monomer ratio, inherent viscosity and/or porosity as to erode and produce lactic acid and glycolic acid continuously for the intended period of device operation.

In addition to the exemplary aspects and embodiments described above, further aspects and embodiments will become apparent by reference to the drawings and by study of the following descriptions.

BRIEF DESCRIPTION OF THE DRAWINGS

FIGS. 3A-3B illustrate another embodiment of an implantable device, with the device shown in exploded view (FIG. 3A) and in assembled view;

FIGS. 4A-4B illustrate another embodiment of an implantable device in exploded view (FIG. 4A) and in assembled view (FIG. 4B), and an approach for inserting a porous partition in one or both ends of the device;

DETAILED DESCRIPTION

I. Definitions

Figure 1:
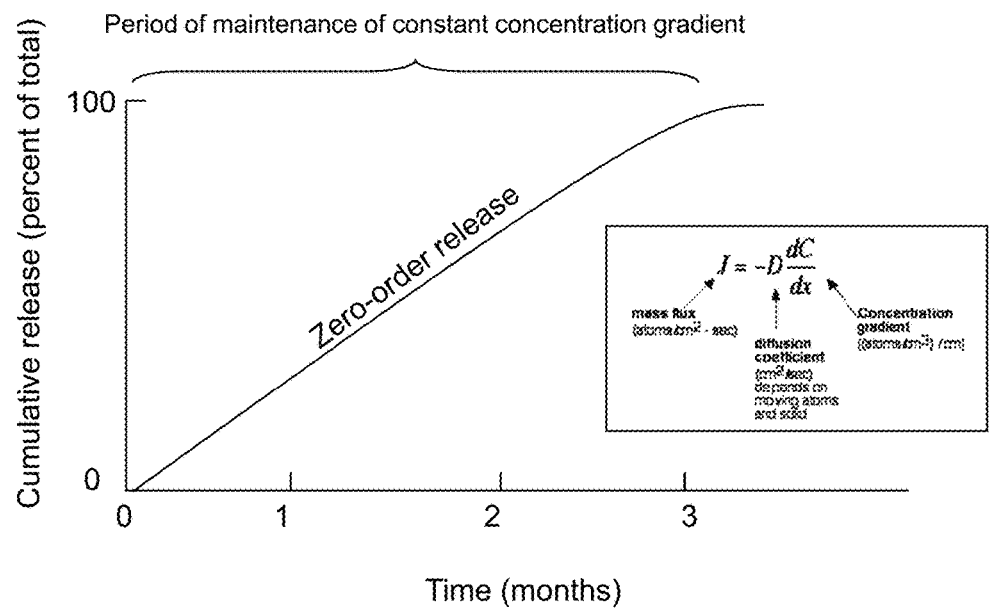
FIG. 1 is a graphic representation of the theoretical relationship between the release kinetics of an agent (rate over time and kinetic order) and the maintenance of a concentration gradient. Concentration of the agent is maintained approximately constant in an internal reservoir by balancing the flux rate and dissolution rates of the agent.

The term "aqueous suspension" refers to a solid material dispersed in a liquid solution that is substantially water.

The terms "therapeutic agent," "drug," "active pharmaceutical ingredient" or "API" refer to a biological or chemical agent used in the treatment of a disease or disorder, or to treat or alleviate symptoms associated with a disease or disorder.

The term "silicon nanopore membrane" means a membrane that has been fabricated, for example, using micromachining techniques borrowed from the microelectronics industry.

The term "precipitate" or "insoluble form" refer to a solid substance that separates from a solution.

A therapeutic agent is "relatively insoluble in water" or "sparingly soluble in water" if its equilibrium solubility in water, measured at room temperature, is less than about $1 \times 10^{-3}$ M.

The term "solubility-modifying agent" refers to an excipient added to the drug suspension formulation and which acts to increase the aqueous solubility of the drug.

The term "substantially zero-order kinetics" means that over a medically acceptable percentage of the dose of a therapeutic agent provided in a drug delivery device, the rate of release of the agent is approximately constant.

II. Drug Delivery Device

In a first aspect, a device for use in releasing a therapeutic agent into an environment of use is provided. The therapeutic agent is preferably one that is sparingly soluble in water. The device, for reasons described hereinbelow, is capable of providing a substantially constant release rate of the drug over an extended time period. The device is particularly well suited to deliver agents which are sparingly soluble in water at neutral pH but become more water soluble at acidic pH. The device also allows delivery of agents which although slightly water-soluble do not generate the concentration gradient sufficient to drive outward flux of a therapeutic dose of the agent. The device is of a size, shape and surface properties to be suitable for subcutaneous implantation and explanation. The device includes an interior chamber separated from an external medium in an environment of use by a porous partition, and contained within the chamber when the device is in use, is an aqueous suspension of the drug mixed with an excipient that generates acidic equivalents. The appearance of these acidic moieties effectively lowers the pH within the reservoir, and, in turn, improves the solubility of the drug. In one general embodiment, the excipient is a degradable polymer, and the continuous hydrolysis of the polymer provides substantially constant release rate of the agent by maintaining a constant solution concentration of the agent in the chamber over a major portion of the extended period of time, and thus providing a sufficient concentration gradient between the chamber and the external medium to produce outward diffusion of the agent across the porous partition at a rate that provides a therapeutic level of agent over the intended period of device operation.

FIG. 1 illustrates the relationship between the percent of total drug loaded into a drug delivery device (including both soluble and insoluble forms) as a function of time. As shown, as long as the concentration gradient is maintained, the output rate is constant (i.e., zero-order). The insert in FIG. 1 presents Fick's law of diffusion and illustrates that the flux (i.e., the outward movement of the agent) is directly proportional to the concentration of the agent.

A. Drug Delivery Device Components and Assembly

Figure 2:
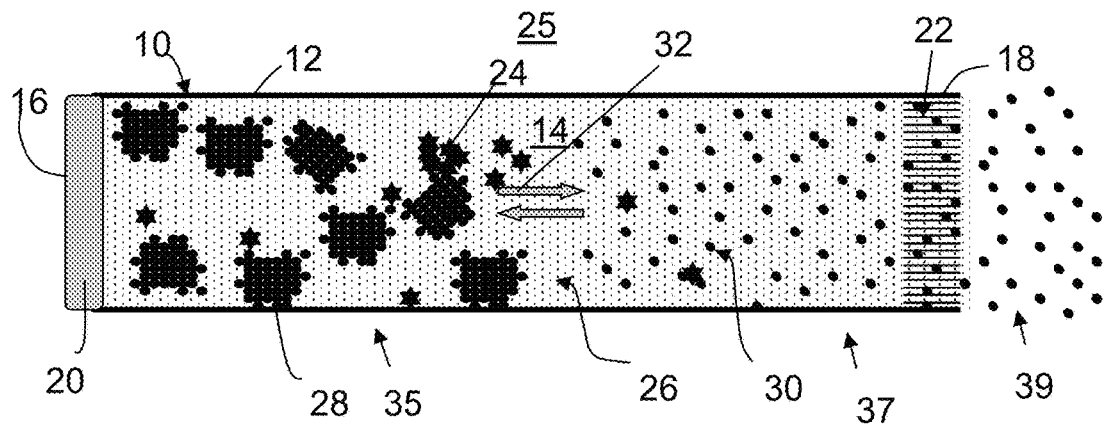
FIG. 2 is an illustration of one embodiment of an implantable drug delivery device prepared for operation according to the principles described herein.

Turning now to FIGS. 2-5 several exemplary embodiments of an implantable drug delivery device for continuous delivery of a drug for an extended period of time are illustrated. With initial reference to FIG. 2, a device 10 intended for implantation in an anatomical compartment of a subject, such as under the skin or in the peritoneal cavity, is illustrated. The device is comprised of a housing member 12 that defines an internal compartment or reservoir 14. Contained within the reservoir is a drug formulation, described below. Housing member 12 has first and second ends, 16, 18. First end 16, in the device embodiment illustrated in FIG. 2, is sealed with a fluid-tight end-cap 20. Opposing second end 18 is fitted with a porous partition 22. It will be appreciated that a porous partition can be positioned at one or both ends of the housing member. As used herein, the terms "porous membrane" and "porous partition" intend a structural member that has a plurality of pores in the micrometer (μm) range, preferably in the 0.1-100 μm range. That is, the porous partition permits passage of the drug in soluble form from the drug formulation contained within the reservoir. The porous partition can also permit passage of a solubility-modifying excipient that is part of the drug formulation, discussed below, in its soluble form. The porous partition in a preferred embodiment retains the drug and/or the solubility-modifying excipient in their insoluble forms. That is, drug and/or solubility-modifying excipient in insoluble form preferably do not pass through the pores of the porous partition.

Housing member 12 is preferably formed from a biocompatible material, and a skilled artisan will readily identify suitable materials, including but not limited to metals, such as titanium, and polymers. A preferred shape of the housing member 12 is cylindrical. Skilled artisans, however, will understand that alternative geometrical shapes may also be suitable, and these shapes are contemplated. In one embodiment, a tubular section of the cylindrical housing member has a non-porous, smooth, and/or liquid impermeable outer surface. For example, a tubular section of housing member 12 formed of titanium and finished on its outer surface, i.e., the surface of device 10 in contact with the environment of use 25, has a satin, mirror, or other polish. To insure the safe and medically uncomplicated use, and removal, of the device, it is preferred that its outer surface be smooth, devoid of pits, ridges and pores. Rough or porous surfaces may tend to provoke a tissue response during the implantation period; tissue in-growth, attachment or adherence of matrix components or cellular processes or pseudopodia to pits or pores on the surface of the device can complicate removal and possibly even tear the ingrown tissue upon removal, causing trauma to the site. Smooth surfaced cylindrical devices, on the other hand, provoke little or no tissue in-growth, are easily removed from the implantation site by simply reopening the incision made during implantation and pushing the distal end of the device with one's fingers through the skin, forcing the device to emerge from the incision. Accordingly, in one embodiment, the housing member is non-porous, and in other embodiments is water-impermeable, non-erodible and/or non-swelling.

Drug formulation 14 contained within the reservoir of the device is preferably in the form of a continuous aqueous phase 26 which may include a solubility-modifying excipient 24 in soluble form, insoluble form, or a mixture of soluble form and insoluble form. The drug formulation includes an active ingredient or drug, examples of which are given below, within the continuous aqueous phase. The drug is present in both insoluble form, as represented by particle 28, and soluble form, as represented by 30. Equilibrium is established between the soluble and insoluble forms of the drug within the drug formulation contained in the reservoir, as indicated by arrows 32. The relative mass of drug present in soluble and insoluble forms depends on its intrinsic solubility in the continuous aqueous phase, which may include a solubility-modifying excipients, the pH and the temperature.

As mentioned, device 10 is intended to be implanted into an anatomical site in a subject, and preferably in implanted at a subcutaneous site. Following implantation, the concentration of the drug in the external medium 25 is maintained at virtually zero at all times by the continuous movement of interstitial fluid around the device. In operation, a concentration gradient is established between the soluble form of the drug or agent within the reservoir and the external medium. The gradient serves to drive diffusion of the soluble form of the agent from the reservoir through the porous partition into the external medium. Equilibrium is established between the insoluble fractions, generally indicated at 35, and soluble fraction of the agent, generally indicated at 37, within the reservoir and a released fraction, indicated at 39, which enters the external medium and is immediately washed away into the systemic circulation. As the soluble form of the agent moves from the device reservoir, through the porous partition and into the external medium under the influence of the concentration gradient, insoluble agent in the formulation contained in the device reservoir dissolves, replacing that which has been released. In this manner a constant concentration gradient is maintained and a constant outward flux of agent is maintained according to Fick's law.

The diffusive flux, J, in mass/unit time, of a molecule through a membrane is defined by Fick's law as follows:

$$J = D_{eff} \cdot A_{eff} \cdot \frac{(C - C_0)}{L} \quad (1)$$

wherein
$D_{eff}$=effective diffusion coefficient, cm²/sec
$A_{eff}$=effective Membrane area, cm²
$C$=concentration of diffusing species on one side of membrane, mass/cm³
$C_0$=concentration of diffusion species on opposite side of membrane
$L$=thickness of membrane, cm.

The effective membrane area is further given as follows:

$$A_{eff} = \varepsilon A_m / 100 \quad (2)$$

wherein
$\varepsilon$=porosity of the membrane, %
$A_m$=physical membrane area, cm²

At constant temperature and for a typical type of porous partition (also referred to herein as a microporous membrane), $D_{eff}$ in Equation (1) is normally a function only of the molecular weight of the diffusing molecule and in general $D_{eff}$ decreases with increasing molecular weight. Therefore, Equation (1) indicates that for implant applications where $C_0$ is approximately zero as it would be in vivo (sink conditions), providing a nearly constant soluble drug concentration will provide a nearly constant drug diffusion rate from the implantable drug delivery device with specific selected properties (e.g., thickness and porosity) of membrane.

In the delivery devices, a chemical equilibrium between the water-soluble and insoluble forms of the agent is established within the drug reservoir. The porous partition separating the reservoir from the external medium is relatively thin (0.02-0.2 cm), highly porous and, preferably, hydrophilic. During operation the pores fill with the aqueous medium by capillary action; the pores thus provide a route for the passage for the soluble fraction of the agent held in the reservoir to the external environment by a process of diffusion. The pores are sufficiently small as to prevent passage of insoluble drug particles held within the reservoir. In practice, the external medium is interstitial fluid. Thus, after implantation, a concentration gradient is established across the partition; the concentration of the agent in the interstitial fluid is virtually zero whereas the concentration of the agent in the reservoir equals the solubility of the agent within the internal aqueous phase of the suspension. The flux of drug is regulated by balancing the surface area of the partition (porosity) and the equilibrium solubility of the agent within in internal aqueous medium according to Fick's second law of diffusion, wherein the desired output rate in mg/day (J) is defined:

$$J(\text{mg/day}) = \frac{\text{mg}}{8.64 \times 10^4} \times \frac{A_M}{100} \quad (3)$$

wherein $A_M$ represents the surface area (i.e., porosity expressed as percent of the area available for diffusion) of the partition.

The equilibrium aqueous concentration of the agent within the chamber ($C_i$) is adjusted to achieve the desired output rate according to the following equation:

$$C_i = \frac{J \cdot T_M}{D} \quad (4)$$

wherein D is the diffusion constant of the agent; and $T_M$ is the thickness of the partition.

As mentioned above, the reservoir of the device contains an aqueous suspension of a drug. The aqueous suspension within the reservoir is separated from the external environment of use by the porous partition which is freely permeable to water. When placed in the preferred in vivo compartment, the interstitial compartment, the carrier fluid within the reservoir would be in direct communication with interstitial fluid (which flows through the subcutaneous space) through the pores of the porous partition. Interstitial fluid is essentially an ultrafiltrate of blood, containing the same ions, buffers and about 70% of the protein present in blood, but excluding formed elements such as red blood cells. Similarly to blood, the pH of interstitial fluid is precisely regulated to be about 7.4. Interstitial fluid continuously moves through the subcutaneous space. All soluble components held within the reservoir of a device incorporating a porous partition such as the one described herein, including the carrier fluid itself, would be free to diffuse in both directions across the partition. Rapid equilibration of ions and buffers between the interstitial fluid and soluble components of the reservoir would ensue rapidly following implantation. For this reason, water miscible solvents such as dimethylsulfoxide (DMSO) or ethanol are not preferred for use as the carrier fluid; such solvents would diffuse out of the device and be replaced by the inflow of interstitial fluid. Exchange of such a solvent carrier with the aqueous interstitial fluid within the reservoir would change the solubility of the loaded agent, adversely affecting its release rate and thus such water-miscible solvents would be unsuitable. If a water-based carrier fluid is used, regardless of its initial composition and pH, equilibration of all soluble species with those of the interstitial fluid would occur within several hours following implantation. Accordingly, in one embodiment, the reservoir of the device does not include an organic solvent or does not include a water-miscible organic solvent. In another embodiment, the reservoir of the device, and the device itself, do not include an osmotic pump or engine.

FIGS. 3-5 further illustrate the implantable device by a discussion of its assembly. FIG. 3A illustrates implantable drug delivery device 50 in exploded, cross-sectional view. A housing member 52 has a wall 54 with an external surface 56 and an internal surface 58. Housing member 52 is hollow, and defines an internal compartment 60. An exemplary housing member is a titanium alloy tube, which are created by milling/lathing solid titanium alloy material. The rod outer diameter (OD) is about 4.3 mm and the length about 35 mm, in one embodiment. The internal reservoir is formed by drilling/milling out the center of each rod. For the device illustrated in FIG. 3A, a first end 62 of the housing member is open, and sized appropriately to permit additional device parts to be inserted into and through the open end. As seen in FIG. 3A, first end 62 includes a first portion 62a having a smaller outer diameter than the outer diameter of the main portion 62b of housing member 52. A lip or transition 68 smoothly connects the first portion 62a and the main portion 62b.

With continuing reference to FIG. 3A, a second end 64 has an annular rim 66 extending inwards from the inner wall, and is referred to as a rim retention section. The rim retention section has, for example, an inner diameter (ID) of 3.4 mm and a depth of a few hundredths of a mm. The housing member also includes a shoulder 70 directly adjacent the retaining rim. Shoulder 70 has a size wide enough to allow insertion of the device components parts, such as o-rings 72, 74 and a porous partition 76, but small enough to capture and engage a press ring 78 for sealing the o-ring/porous partition/o-ring stack 80 (see FIG. 3B) into place at the second end 64 of the housing member. The ID of the remaining portion of the housing member, that is the portion between shoulder 70 and lip 68, is, in this embodiment, about 3-4.5 mm, more preferably 3-5-4.0 mm, and preferably is 3.8 mm. The internal volume of the device is therefore approximately between 350-400 microliters, more preferably 375-390 microliters, and preferably 380 microliters.

In one embodiment, the porous partition is a conventional porous membrane with pore sizes selected to allow diffusion of the dissolved agent but prevent insoluble material of leaving the device. In another embodiment, the partition may be made using silicon microfabrication techniques which create assays of parallel channels each of which in its smallest dimension is from 1.5 to 5 times the hydrodynamic diameter of the agent itself. When the channel width is properly tailored to the molecular dimensions of the agent, such nanopore membranes have been shown to constrain the diffusion of the agent. Alternatively, the porous partition may be selected from a variety of conventional crosslinked polymer membranes such as those used in ultrafiltration and dialysis applications or crosslinked or polymerized gels such as polyacrylamide, agarose, alginate and the like. Sintered metal membranes or frits composed of titanium, titanium alloys or stainless steels or sintered ceramic membranes and metal screens typically used as in-line filters also may serve as the porous partition. Pore size and/or molecular weight cut-off of the membrane or gel would be selected to substantially retain the insoluble form of the drug within the device reservoir while allowing diffusion of the agent across the membrane. In operation, the rate of diffusion of the agent would be determined by the concentration gradient of the agent across the membrane (i.e., the difference in concentration of the soluble portion of the agent within the chamber and "sink conditions" external to the device) and the cross sectional area (porosity) of the partition (as exemplified in the Equations above). In one embodiment, the total area occupied by the pores contained in the partition is less than about 2 $cm^2$, more preferably less than about 1.7 $cm^2$.

Device 50 is constructed by inserting into the reservoir the two o-rings, 72, 74, with the porous partition 76 sandwiched between the o-rings, as indicated by arrow 90. The porous partition, in this embodiment, is a stainless steel mesh screen or a sintered titanium frit. The o-rings are preferably made of silicone measuring 70 on the Shore A scale, and preferably measure 0.091" inner diameter by 0.026" cross section.

The partition press-ring 78 is then mechanically pressed into place above the o-ring 74, to apply pressure to the o-ring/partition/o-ring stack 80 and seal the o-rings against the inner wall of the housing member, the porous partition and retention rim. In one embodiment, the partition ring is an annular ring with a flat o-ring interface surface. When the o-ring is inserted into the housing member to its proper depth, it engages shoulder 70 of the housing member, forming a fluid-tight seal of the o-ring/partition/o-ring stack 80 with the retaining rim.

After the reservoir is filled with a desired drug formulation, and an exemplary filling procedure is described below, an end-cap 92 with a domed external surface 94, a press surface 96 to interface with the wall of the housing member and form a fluid-tight seal, is pressed onto end 62, as indicated by arrow 98. FIG. 3B illustrates the device with its component parts in place for implantation and operation.

FIGS. 4A-4B illustrate another embodiment of a drug delivery device, in exploded view (FIG. 4A) and fully assembled for use (FIG. 4B). Drug delivery device 100 is comprised of a tubular housing 102 having a wall 104 that defines an internal cavity 106. Housing 102 has opposing ends, 106, 108. Housing 102 has a first outer diameter dimension at opposing ends 106, 108 and a second outer diameter dimension in the portion of the housing between the opposing ends. Transition regions 110, 112 connect the first and second outer dimensions of housing 102. A porous partition, such a porous partition 114, is sized for contact with an annular rim, such as annular rim 115, at each end of the housing. Each porous partition preferably has an outer diameter approximately equal to the first outer diameter at each end 106, 108. A sealing member, such as sealing member 116, is sized for engagement with each porous partition about the rim at each end 106, 108. An end cap, such as end cap 118, is dimensioned for a secure fit around the external surface of the housing at each end. In this embodiment, the end caps each have a central opening, such as opening 120 in cap 118, to permit in-flow of interstitial fluid from the environment of use external to the device into reservoir 106 and efflux of soluble drug from reservoir 106, across the porous partition, and into the environment of use. FIG. 4B shows the device with the porous partitions, sealing members, and end caps in place on housing member 102. As seen, the outer diameters of the end caps are dimensioned for agreement with the a second outer diameter dimension in the portion of the housing between the opposing ends, so that the overall outer dimension of the device when fully assembled is uniform.

Figure 5A:
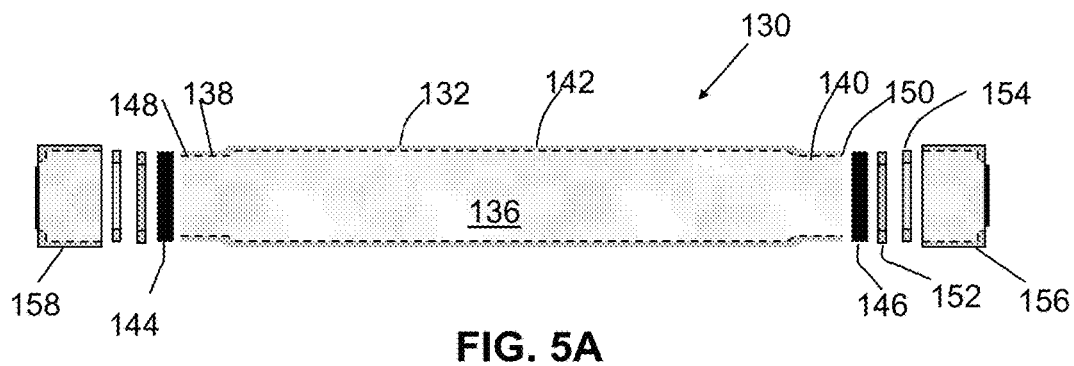
FIGS. 5A-5B illustrate another embodiment of an implantable device in accord with the teachings herein, the device shown in exploded view (FIG. 5A) and in assembled view (FIG. 5B)
Figure 5B:
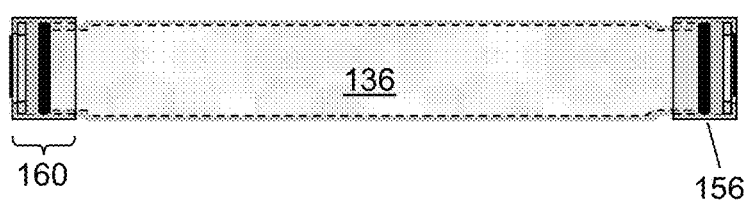

FIGS. 5A-5B illustrate another embodiment of a drug delivery device, in exploded view (FIG. 5A) and fully assembled for use (FIG. 5B). Device 130 comprises an annular encasement 132 have an external surface 134 that is smooth, non-porous, and liquid impermeable. Encasement 132 is hollow, and its wall defines an internal cavity 136 which when assembled for use contains a drug formulation. Each end of annular encasement, ends 138, 140, has a smaller outer diameter than a middle section 142 of the annular encasement. A frit, such as frits 144, 146, are dimensioned for contact with a lip, 148, 150, at each end, frits 144, 146 having a diameter approximately equal to the outer diameter of ends 138, 140. The frits can be of ceramic, glass, or metal and are permeable to soluble drug in the drug formulation. A polymer membrane, such as membrane 152, abuts each frit and is in dimensional agreement with the frits. The polymer membrane can be porous or non-porous, so long as it is permeable to solubilized drug and fluid in the environment of use. An o-ring or similar sealing member, such as member 154 provides sealing engagement of the frit, membrane, and a press cap, such as press caps 156, 158. Together the frit, polymer membrane, and o-ring at each end of the device form a stack, such as stack 160, that is held in place at each end by the press caps. Each press cap has a central opening, for fluid communication between the cavity of the device and the environment of use.

The internal reservoir of the drug delivery device is filled with a drug formulation. The formulation is comprised of a drug (also referred to as a therapeutic agent), a solubility-modifying agent, an aqueous continuous phase. The therapeutic agent used in the device may be a small molecular weight drug, preferably having an equilibrium solubility constant of between about $1\times10^{-3}$ M and $5\times10^{-3}$ M at 37° C. in the aqueous continuous phase. In a preferred embodiment, the formulation in the device reservoir comprises an aqueous suspension of a drug that is sparing soluble in water. The term 'sparingly soluble', as used herein, refers to a drug having a solubility measured in water at 37° C. of less than about 3 mg/ml at neutral pH, preferably of between about 0.001 to 3 mg/mL, or 0.025 to 3 mg/mL, at neutral pH. More generally, sparingly soluble drugs for use in the device described herein have a solubility in water at 37° C. of less than about 3 mg/mL at neutral pH, and have an increasing solubility as pH decreases, as discussed further below. Since diffusion is driven by the concentration gradient established across the porous partition in the device, as discussed above, drugs with low solubility in water at physiological pH do not achieve a concentration gradient sufficient to provide release of a therapeutic dose of the drug.

In another embodiment, drugs for use with the device described herein have a therapeutic dose of less than about 3 mg/day, preferably of less than about 2.5 mg/day, and still more preferably of less than about 2 mg/day or 1.5 mg/day.

Non-limiting examples of drugs includes neuroleptic agents, such as risperidone and olanzapine. Neuroleptic agents are prescribed for the treatment of psychotic disorders such as schizophrenia and bipolar disorder. The desired dose, or release rate, for neuroleptic agents is 0.5-3 mg/day, more preferably 1-2 mg/day, for a period of between about 1-3, 1-4, 1-5, or 1-6 months. Another class of exemplary therapeutic agents is the low-solubility opioid mixed agonist-antagonists, such as buprenorphine, which is used to treat chronic pain, opioid addiction and alcoholism. Other sparingly-soluble drugs are paliperidone, aripiprazole, asenapine and haloperidol. These drugs, and especially risperidone, olanzapine and buprenorphine, have low aqueous solubility at physiological pHs, on the order of $1\times10^{-3}$ M to $5\times10^{-3}$ M.

Figure 6:
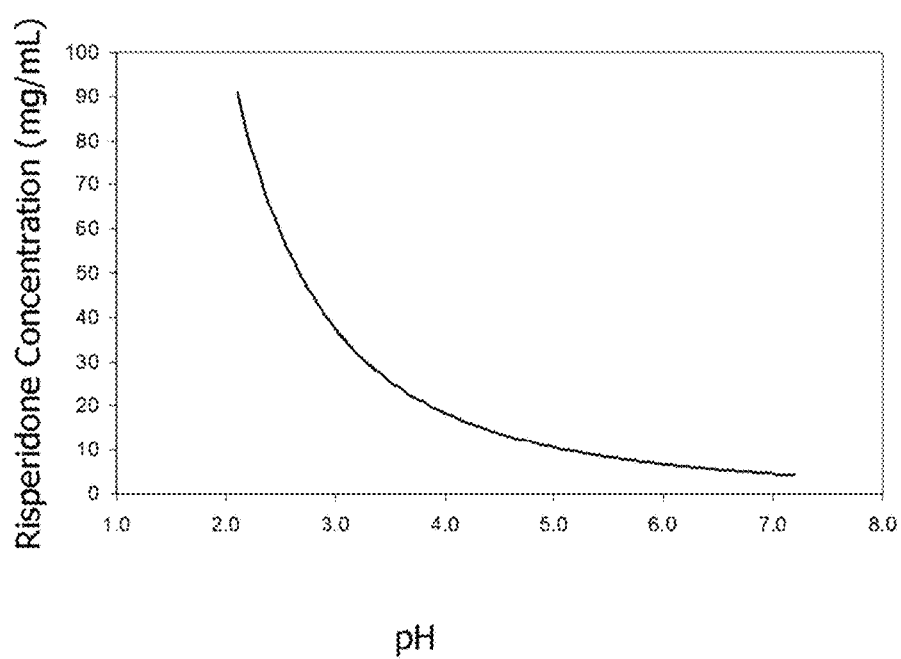
FIG. 6 is a projection illustrating the approximate relationship between pH and the aqueous solubility of risperidone base.

It is possible to adjust the pH of a drug suspension within a reservoir device that is separated by a porous partition from the external medium to virtually any desired level and thus regulate the initial equilibrium solubilities of drugs, such as risperidone. In the case of risperidone, solubility increases several fold as the pH is lowered to 6.0. Indeed by adjusting the internal pH of a risperidone suspension it is possible to raise the aqueous solubility from 0.4 mg/mL at pH 7.4 to about 100 mg/mL at pH 2.0, as shown in FIG. 6. For the device described herein, adequate drug release rates would be possible at pH's below about 6.0. In practice, however, following implantation, exchange of buffers across the partition (which is freely permeable both to water and small molecules), between the aqueous phase of the drug formulation held in the reservoir of the device and the external interstitial fluid, would cause the internal pH of the drug formulation to quickly equilibrate to 7.4, regardless of its initial pH. Accordingly, the drug formulation additionally comprises an insoluble excipient capable of continuously generating acid groups during operation of the device, effectively decreasing the pH of the drug formulation within the device reservoir to maintain a pH that increases the aqueous solubility of the drug to a level which provides a concentration sufficient to drive outward diffusion required to achieve a therapeutic in vivo release rate for a period of at least about 1 month, 2 months, or 3, 4, 5, or 6 months.

In one embodiment, the insoluble excipient, also referred to herein as a solubility-modifying excipient, is a polymer. Reference to polymer preferably includes copolymers. "Copolymers" are polymers formed of more than one polymer precursor. Polymers preferred for use in the drug formulation are those which are prepared from precursors that, in a preferred embodiment, are soluble in a solvent that is soluble in an antisolvent and can be polymerized with light initiation. One class of such polymers includes those that are degradable, preferably biodegradable. Another class of polymers includes poly lactic acids. In a preferred embodiment, the polymers are degradable or erodible. Degradable or erodible polymers are those that degrade upon exposure to some stimulus, including time and exposure to aqueous media. Degradable or erodible polymers include biodegradable polymers. Biodegradable polymers degrade in a biological system, or under conditions present in a biological system such as an aqueous medium. Preferred biodegradable polymers degrade within the device described herein following the introduction of an aqueous medium. Examples of biodegradable polymers include those having at least some repeating unit representative of at least one of the following: an alpha-hydroxycarboxylic acid, a cyclic diester of an alpha-hydroxycarboxylic acid, a dioxanone, a lactone, a cyclic carbonate, a cyclic oxalate, an epoxide, a glycol, and anhydrides. Preferred degradable or erodible polymers comprise at least some repeating units representative of polymerizing at least one of lactic acid, glycolic acid, lactide, glycolide, ethylene oxide and ethylene glycol.

Another class of suitable polymers are biocompatible polymers. One type of biocompatible polymers degrades to a nontoxic acidic product. Specific examples of biocompatible polymers that degrade to nontoxic products that do not need removal from biological systems include poly(hydro acids), poly (L-lactic acid), poly (D,L-lactic acid), poly (glycolic acid) and copolymers thereof. Polyanhydrides have a history of biocompatibility and surface degradation characteristics (Langer, R. (1993) Acc. Chem. Res. 26:537-542; Brem, H. et al. (1995) Lancet 345:1008-1012; Tamada, J. and Langer, R. J. (1992) J. Biomat Sci.-Polym. Ed. 3:315-353).

Figure 11:
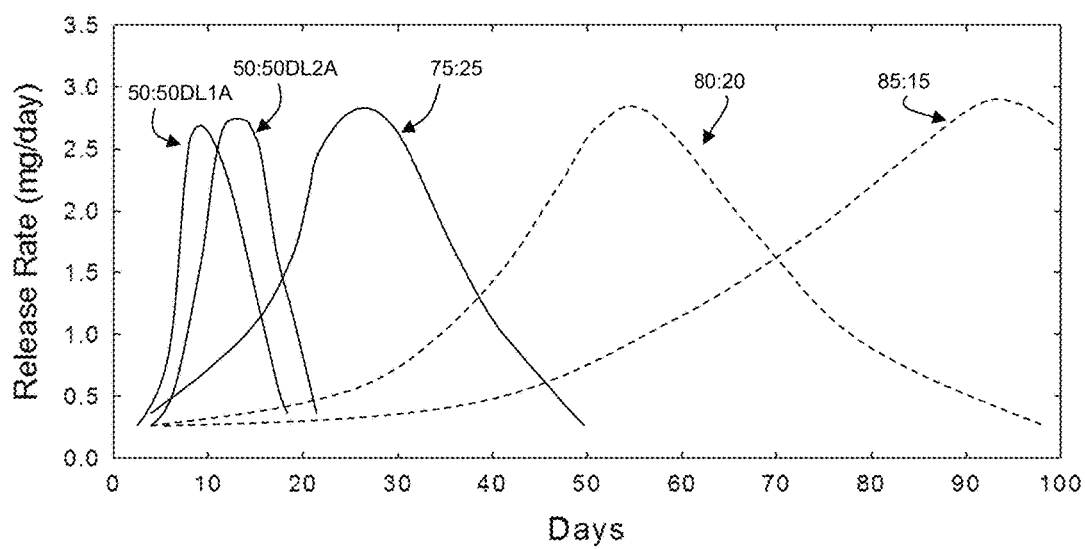
FIG. 11 is a graph of risperidone release rate, in mg./day, as a function of time, in days, where the series of curves illustrates the influence of the solubility-modifying agent PLGA with different lactic acid:glycoloic acid ratios on the in vitro release of risperidone.

Poly(lactic-co-glycolic acid) (PLGA) is a copolymer prepared by co-polymerization of two different monomers, the cyclic dimers (1,4-dioxane-2,5-diones) of glycolic acid and lactic acid. During polymerization, successive monomeric units of glycolic or lactic acid are linked together by ester linkages, thus yielding a linear, aliphatic polyester as a product. Depending on the ratio of lactide to glycolide used for the polymerization, different forms of PLGA can be obtained. These forms are usually identified in regard to the monomers' ratio used, e.g. PLGA 75:25 identifies a copolymer whose composition is 75% lactic acid and 25% glycolic acid. PLGA degrades by hydrolysis of its ester linkages in the presence of water. The time required for degradation of PLGA is related to the monomers' ratio used in production, where the higher the content of glycolide units, the lower the time required for degradation, other than a copolymer with a 50:50 monomeric ratio of lactide and glycloide, which exhibits degradation in an aqueous environment in about two months. PLGA copolymers that are end-capped with esters (as opposed to the free carboxylic acid) demonstrate longer degradation half-lives. PLGA is a biodegradable polymer because it undergoes hydrolysis in the body to produce the original monomers, lactic acid and glycolic acid. These two monomers under normal physiological conditions, are by-products of various metabolic pathways in the body. Since the body effectively deals with the two monomers, there is very minimal systemic toxicity associated with using PLGA for drug delivery or biomaterial applications. The possibility to tailor the polymer degradation time by altering the ratio of the monomers used during synthesis lends this polymer particularly suitable for the device herein, as further illustrated below (FIG. 11). A skilled artisan, however, will appreciate that other biodegradable polymers are similarly beneficial for use as the solubility-modifying excipients, including polycaprolactone, polyglycolide, polylactic acid, and poly-3-hydroxybutyrate.

An exemplary approach for filling a drug delivery device reservoir with a drug formulation is now provided. The device, fitted at one end with a stainless steel or sintered titanium porous partition or polymeric membrane, is weighed (including the end cap) to obtain a tear weight and positioned in a holder with the partition end down. A known amount of drug, e.g., approximately 100 mg of risperidone (free base) powder (Ren-Pharm Intl, particle size 2-100 micrometers), is filled into each reservoir. The powder may be filled by any known powder filling approaches and may be packed into the reservoir using a blunt 3.7 mm stainless steel rod. A drug/solubility-modifying agent mixture could also be introduced as a solution in a volatile solvent such as ethanol. Incremental introduction of the solution into the reservoir with concomitant removal of the solvent, by for example elevated temperature, a stream of nitrogen, or reduced pressure, is another approach. A solid or semi-solid mixture of drug and solubility-modifying agent can also be extruded into the reservoir by standard methods known in the art. Following filling with dry drug, the open end of the reservoir is sealed using a mechanically pressed-on end-cap described above and the reservoir reweighed and the drug fill weight calculated. Alternatively, the open end can be fitted with a second porous membrane to increase (double) the effective surface area available for diffuse release of the drug, as illustrated in FIGS. 4-5.

The aqueous suspension, in one embodiment, is made by mixing a crystalline, amorphous, freeze-dried, spray dried or otherwise dried powder, pellets or micronized powder of the agent (or the agent co-mixed as a physical mixture, melt or fusion mixture or with various bulking agents and excipients known in the art), and solubility-modifying excipients with the internal aqueous medium under conditions designed to achieve the desired concentration gradient. A small portion of the dry agent dissolves in the aqueous solution at once, while the bulk remains in insoluble suspension form. Initially, only the small proportion of the total amount of agent filled into the internal reservoir that dissolves in the internal aqueous phase is available to diffuse out of the chamber through the porous partition. As the soluble form of the agent diffuses out of the reservoir through the partition into the external medium, it is replaced by the dissolution of the insoluble form within the reservoir. The balance between the exit of the initially dissolved agent and the continuous process of dissolution of the insoluble agent maintains a nearly constant concentration of soluble agent within the device reservoir.

At small scale production, the membrane-end of each reservoir is inserted into a tube connected to one end of a 3-way valve. The connection is sealed using an o-ring selected to fit around the reservoir housing and screw-cap compression fitting. A syringe filled with phosphate buffered saline (PBS, pH 7.4) is attached to a second port of the three-way valve. The third port is connected to a vacuum source. Initially, the valve is positioned so that the reservoir is connected to the vacuum source and the air in the reservoir is evacuated for 10 minutes. The valve is then positioned so that the evacuated, dry, drug-loaded reservoir is connected to the syringe containing buffer. PBS is drawn into the evacuated reservoir under reduced pressure created during the vacuum step, instantly creating a drug suspension in situ within the reservoir. A removable cap is fixed to the membrane end of the reservoir until used.

For single devices fitted with membranes on each end, the device is first placed in a cylindrical tube with a slightly larger inner diameter than the outer diameter of the device and a slightly longer overall length. The tube is capped and sealed on one end. The open end of the tube is then connected to the to the 3-way valve, evacuated and back-filled with buffer as described above. Alternatively multiple devices may be placed in a larger chamber or manifold system and similarly filled with buffer following evacuation of the chamber under vacuum.

In larger scale production, individual drug-loaded, sealed reservoirs are placed in 13 mm neck borosilicate glass lyophilization vials designed to hold each device. The vials are loosely fitted with a lyophilization stopper and placed in a vacuum oven equipped with mechanically movable shelves. The vials are heated at 140° C. for 30 minutes to terminally sterilize the systems. After return to ambient temperature, a vacuum is applied for 24 hours at which time the vials are sealed in vacuo by raising the shelf and fully seating the stoppers. Stoppers are affixed to the vials with removable aluminum crimps. Vials are inspected, labeled and stored for use at room temperature.

B. Drug Delivery Device Performance: In Vitro Release

In one embodiment, the device is configured for, operable to, and/or capable of delivering a sparingly soluble therapeutic agent at a constant release rate for a period of at least about 1, 2, 3, 4, 5, 6, 7, 8, 9, 10, 11, or 12 months, preferably, in one embodiment, at a zero-order release rate. In vitro and in vivo performance of devices, prepared as described above, and capable of such delivery is now described.

As described in Example 1, typical Franz-type diffusion cells were fitted with a porous partition separating a donor chamber from a receptor chamber. The partitions were selected to span a wide range of pore sizes (i.e., molecular weight cut-off or "MWCO", values or nominal pose diameter) The porous partitions selected for use in this study had molecular weight cut-off values of 100,000 Daltons and 3,000 Daltons. In addition, a porous partition in the form of a 0.45 μm polyvinyldenefluoride membrane filter (Durapore®) was used. A drug formulation in the form of an aqueous suspension comprising risperidone, as a model for a sparing soluble therapeutic agent, a solubility-modifying excipient PLGA (polylactic ploy glycolic acid co-polymer), a biodegradable, biocompatible copolymer, was prepared and placed in the donor chamber. Release of risperidone from the formulation into the receptor chamber was measured as a function of time, and the results are shown in FIGS. 7A-7B.

Figure 7A:
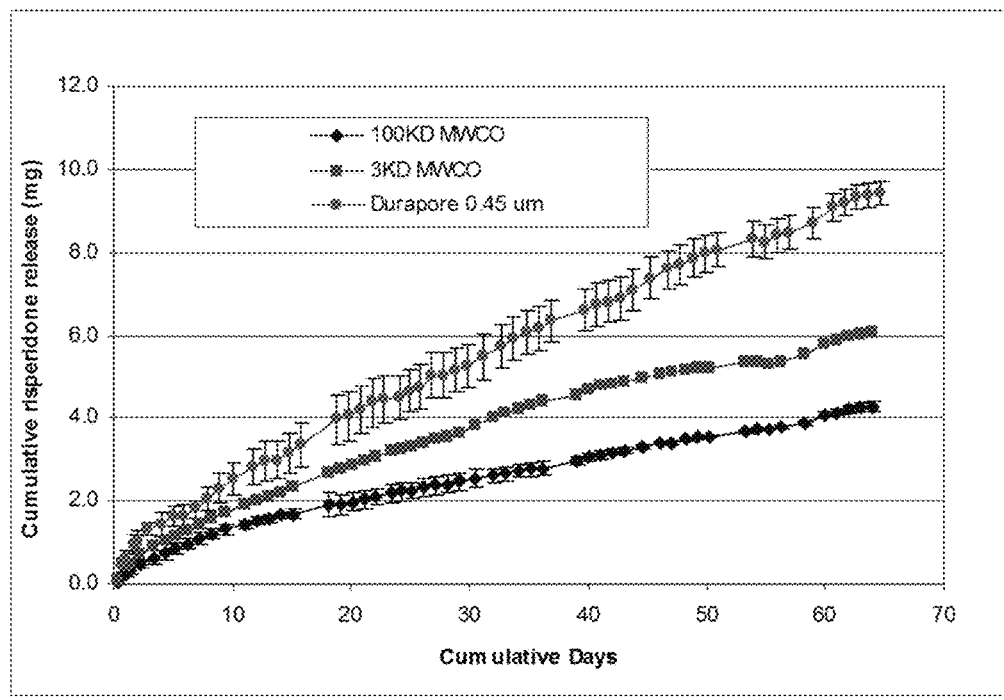
FIGS. 7A-7B are graphs showing cumulative release of risperidone in vitro, in mg (FIG. 7A), and the release rate of risperidone, in mg/day (FIG. 7B), as a function of time, in days, from devices having a porous partition separating the drug formulation from the environment of use, the porous partition in the devices had a molecular weight cut-off (MWCO) of 100 KD (triangles) or 3 KD (squares) or was a 0.45 μm polyvinyldenefluoride membrane filter (Durapore®; circles)
Figure 7B:
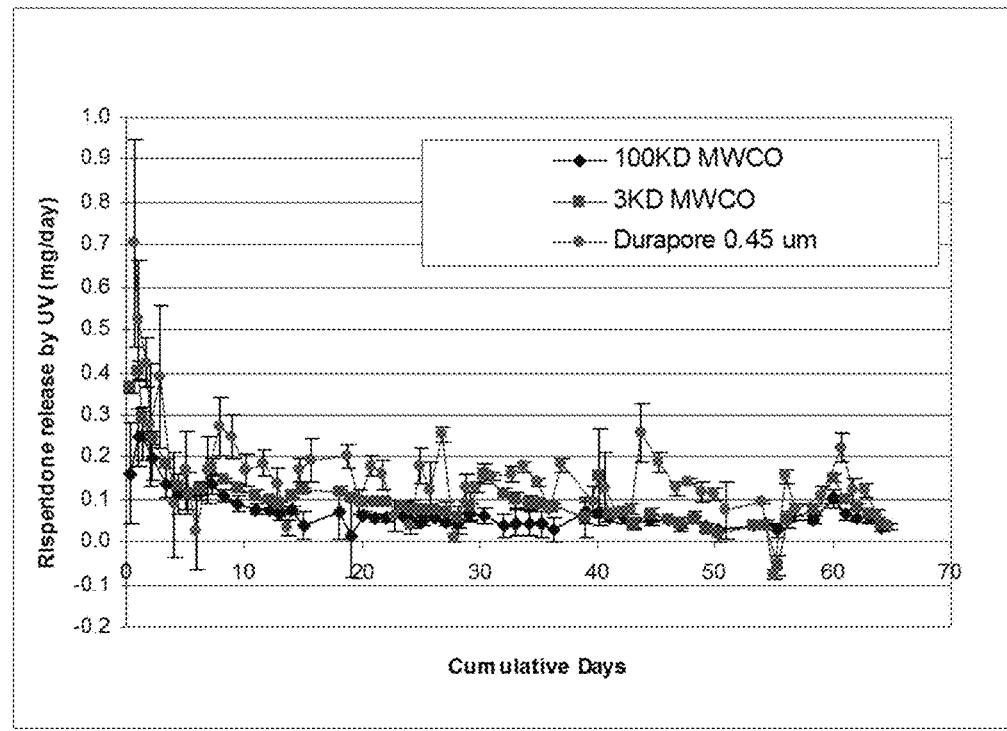

FIGS. 7A-7B are graphs showing cumulative release of risperidone in vitro, in mg (FIG. 7A), and the release rate of risperidone, in mg/day (FIG. 7B), as a function of time, in days. Sustained, substantially zero-order release rate was obtained, as best seen in FIG. 7B. Risperidone was released from the devices with the porous partitions of 100,000 Dalton molecular weight cut-off (triangles), 3,000 Dalton molecular weight cut-off (squares), and the 0.45 μm polyvinyldenefluoride membrane filter (circles) at rates of 200 μg/day, 100 μg/day and 70 μg/day, respectively, were achieved following a short 3-4 day equilibration phase.

The aqueous solubility of many sparingly soluble drugs, such as risperidone, increases as the pH is lowered to below that characteristic of physiological fluids (i.e., pH of 7.4). Risperidone is only sparingly soluble in water at pH 7.4 (~0.42 mg/mL). Assuming a risperidone concentration of 0.42 mg/mL, a pore area (A) of a 3.5 mm partition is 0.09 cm², that two such partitions are used at each end of a drug delivery device as described herein to provide a total diffusional area of 2×A, that a diffusion constant of glucose is 7.0×10⁻⁶, and that the thickness of the partition is 0.12 cm, Fick's law can be used to determine the rate of efflux, J, as follows:

$$J = A\left(D \cdot \frac{C}{T}\right) \tag{5}$$

$$J = 0.01 \text{ cm}^2 \left(7 \times 10^{-6} \text{cm}^2 \text{sec}^{-1} \times \frac{0.42 \text{ mg} \cdot \text{ml}^{-1}}{0.12 \text{ cm}}\right) \tag{6}$$

$$J = 0.012 \text{ mg} \cdot \text{day}^{-1} \tag{7}$$

This rate of efflux is well below the risperidone dose needed to provide human therapeutic effects. An in vitro rate of about 1-2 mg/day would be needed to achieve a therapeutic effect. To adjust the solubility of risperidone to a concentration within the device that would provide an efflux rate of between about 1-2 mg/day it would be necessary to increase the internal concentration of soluble risperidone to 1-2 mg/mL. Therefore, solubility enhancement of the sparingly soluble drug is needed to achieve a release rate from the device that provides a therapeutic dose. One approach is to lower the pH of the aqueous suspension in the device. For example, at pH 6.8 the equilibrium concentration of risperidone is about 1.5 mg/mL (see FIG. 6). At this concentration in the example given above the output rate would be in therapeutic range. But, since the device reservoir containing the aqueous suspension of drug communicates with the external medium in the environment of use that is filled with interstitial fluid, the pH of which is regulated by buffers (primarily bicarbonate-pCO₂) to be 7.4, it is inevitable that the internal pH of the device would equilibrate to pH 7.4 quickly following implantation, regardless of the initial pH of the internal aqueous phase. The present device is based on a discovery that circumvents this dilemma. Inclusion of a solubility-modifying excipients capable of generating acid groups for a sustained period of time maintains a pH of the aqueous suspension in the device that provides a solubility of the drug sufficient to achieve a therapeutic rate of release from the device for a sustained period of time. In one embodiment, the solubility-modifying excipients is a biocompatible, biodegradable co-polymer of poly-lactic and poly-glycolic acids (PLGA). The PLGA effectively lowers the internal pH of the aqueous suspension, as the polymer erodes and releases acid groups, free lactic and glycolic acids, respectively. The continual release of acid groups increases the solubility of the drug in the aqueous suspension, and provides increased release rates despite the pH of external buffer being maintained at pH 7.4.

Figure 8:
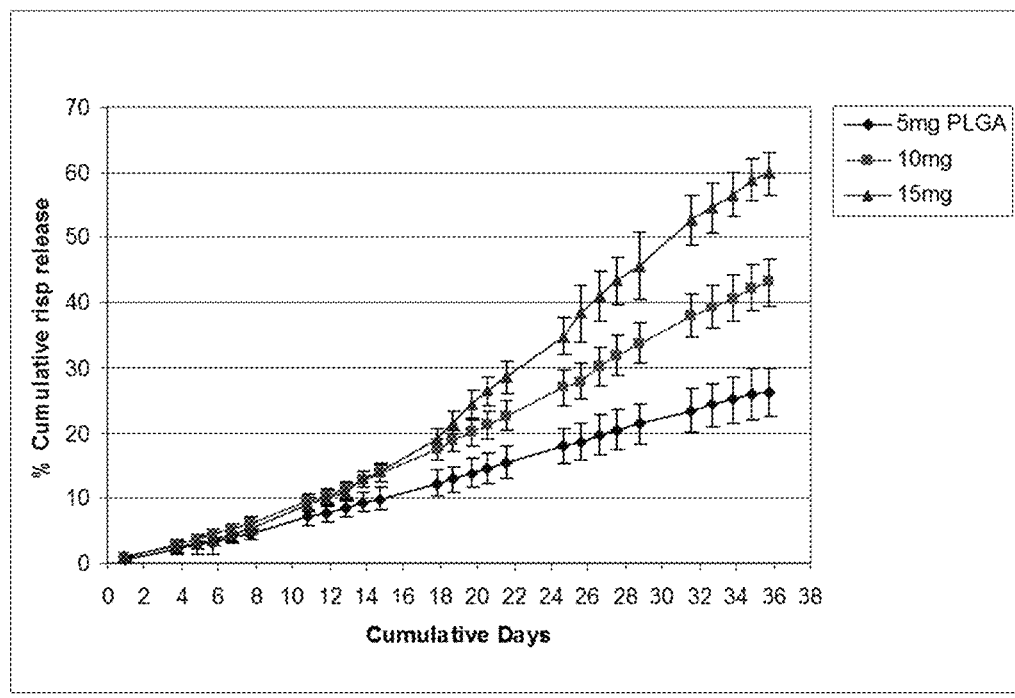
FIG. 8 is a graph of the cumulative release of risperidone, as a percent of total amount of risperidone in the device, as a function of time, in days, where the risperidone in the device was an aqueous solution comprising 5 mg (diamonds), 10 mg (squares) or 15 mg (triangles) poly-lactic-poly-glycolic acid (PLGA)
Figure 9:
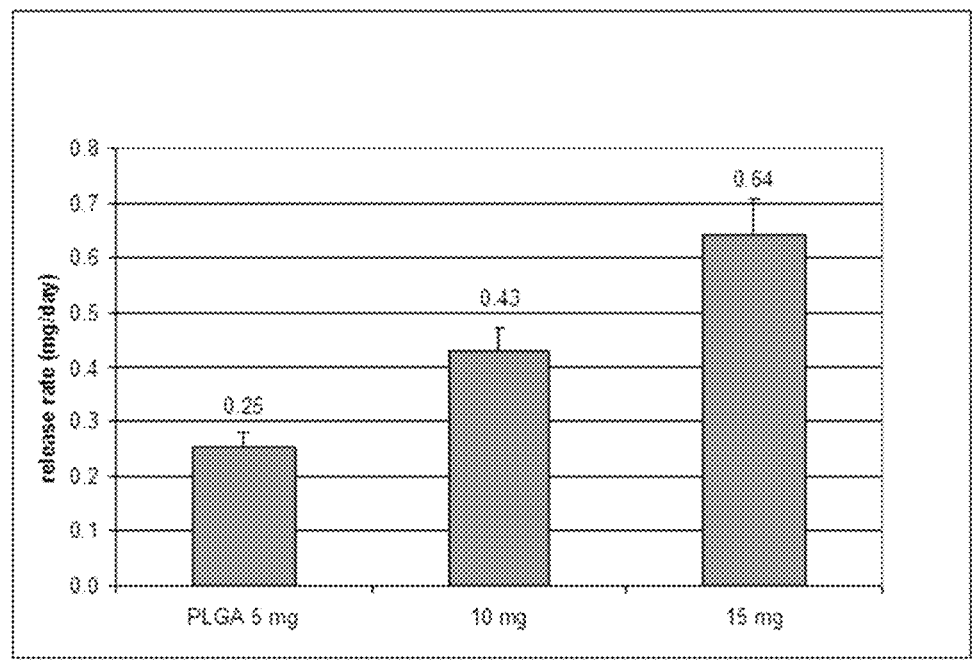
FIG. 9 is a bar graph showing the dose-response relationship between risperidone release rate, in mg/day, and amount (5 mg, 10 mg, 15 mg) of a solubility-modifying agent (85:15 PLGA) added to the aqueous drug suspension loaded into the device.

This effect is illustrated by the study described in Example 3, where release of the sparingly soluble drug risperiodone, as a model of all sparingly soluble drugs, from aqueous suspensions comprising various amounts of PLGA was measured as a function of time. As seen in FIG. 8, addition of 5 mg (diamonds), 10 mg (squares) or 15 mg (triangles) of 85:15 PLGA to the aqueous risperidone suspension contained in the reservoir of the devices provided a dose-dependent increase in drug release rate. Drug formulations with 15 mg PLGA (triangles) yielded a release rate that approached about 0.6 to 1.0 mg/day. Drug delivery devices with increasing amounts of solubility-modifying excipient PLGA from 5 mg, 10 mg to 15 mg, gave a linear increase in release rate, from 0.25 mg/day to 0.43 mg/day to 0.64 mg/day, as seen in FIG. 9. Doubling the amount of solubility-modifying excipient PLGA doubled the release rate.

Further studies were done to evaluate the type and combinations of solubility-modifying excipients. As discussed above, PLGA is prepared by co-polymerization of two different monomers, glycolic acid and lactic acid. The ratio of lactide to glycolide used in the synthesis yields different forms of PLGA. A study was conducted to evaluate the release rate of a sparingly-soluble drug from devices as described herein using various types of PLGA. As described in Example 3, aqueous suspensions of risperidone five different PLGA co-polymers were prepared. The three co-polymers were 50:50 poly(dl-lactide-co-glycolide-1A), 50:50 poly(dl-lactide-co-glycolide-2A) and 85:15 poly(dl-lactide-co-glycolide). Results are shown in FIG. 11.

FIG. 11 shows the risperidone release rate, in mg/day, as a function of time, in days, for devices filled with the various drug formulations. The series of curves illustrate the influence of the solubility-modifying agent PLGA with different lactic acid:glycoloic acid ratios on the in vitro release of risperidone. The first two curves in FIG. 11 show the release of risperidone from an aqueous suspension comprising a 50:50 PLGA (DL1A and DL2A). The third curve shows the release of risperidine from an aqueous suspension comprising 85:15 PLGA. The fourth and fifth curves illustrate the projected release of risperidone from an aqueous suspension comprising PLGA with ratios of 90:10 and 95:5, respectively. The data and projections presented in FIG. 11 illustrate that the erosion rate of PLGAs in aqueous media decreases with increasing lactic acid content. Aqueous mixtures of PLGAs of increasing lactic acid content (starting at 50:50) can be selected to generate a constant number of free acid equivalents (lactic acid glycolic acid) over a selected period of time, for example for a period of 2, 3, 4, 5, 6 months or longer. The free lactic acid and glycolic acid equivalents generated by the differential erosion of the various co-polymers in the PLGA co-polymer family increase the solubility of risperidone and thus increase its diffusion rate across the porous partition of the drug delivery device. By selecting mixtures of PLGAs with different, and in one embodiment, overlapping erosion rates, the augmented, free acid-mediated release of a sparingly soluble drug is maintained for a sustained period. In practice, drug delivery devices can be filled with dry powder physical mixtures of risperidone and one or more PLGAs, selected to provide sustained release of the sparingly soluble drug. Following hydration and implantation the PLGAs begin to erode at a rate depending on its ratio of lactic:glycolic acid, continuously generating free acid equivalents which, in turn, elevate the solubility of the sparingly soluble drug within the reservoir and thus sustain its constant release rate from the device. Release rates in the therapeutic range of 1-2 mg/day are achievable for periods ranging from of 1-6 months.

Accordingly, in one embodiment, devices comprising a drug formulation with a solubility-modifying agent are contemplated, wherein the solubility-modifying agent is one or more poly(dl-lactide-co-glycolide) co-polymers, selected to have a glycolide content of less than 15%, preferably less than 10%, more preferably less than 8%, 7%, 6%, 5%, 4%, 3%, 2% or 1%, to achieve a sustained, continuous release of acid groups in the drug formulation, thereby achieving a sustained, zero-order release of a sparingly soluble drug. In one embodiment, the drug formulation is an aqueous suspension comprising the sparingly-soluble drug. That is, the reservoir of the device prior to use comprises an aqueous suspension of the drug and one or more solubility-modifying excipients. In another embodiment, the drug formulation is a dry or dried mixture of the sparingly-soluble drug and the one or more solubility-modifying excipients. In this latter embodiment, the dry drug formulation hydrates subsequent to implantation of the device by in-flow of interstitial fluid across the porous partition.

In another study, described in Example 4, devices were prepared from titanium cylindrical tubes. The reservoir of each device was filled with risperidone free base in the form of a dry powder, and in one group of the devices, a mixture of 50:50 PLGA and 85:15 PLGA was included. The devices were fitted with a porous partition at each end, as illustrated in FIGS. 4A-4B and 5A-5B. Release of risperidone from the devices into a recipient buffer was measured and the results are shown in FIG. 11. As seen, without the added PLGA the devices released risperadone at a rate of less than 0.05 mg/day, far below the therapeutic dose level of >1 gm/day. In contrast, the devices with the added PLGA released risperidone at an average of 1-1.2 mg/day, well within the target therapeutic range.

In yet another study, devices were prepared as described herein an tested in vitro and in vivo. As described in Example 5, devices having a cylindrical titanium housing with an internal reservoir were filled with dry powdered risperidone. One group of the devices additionally included a mixture of 50:50 PLGA and 85:15 PLGA admixed with the risperidone. A subset of each group of devices was tested for in vitro release of risperidone and the other subset implanted subcutaneously into rats. Release of risperidone was determine by taking aliquots of buffer or blood, accordingly. Results are shown in FIGS. 12A-12B.

Figure 12A:
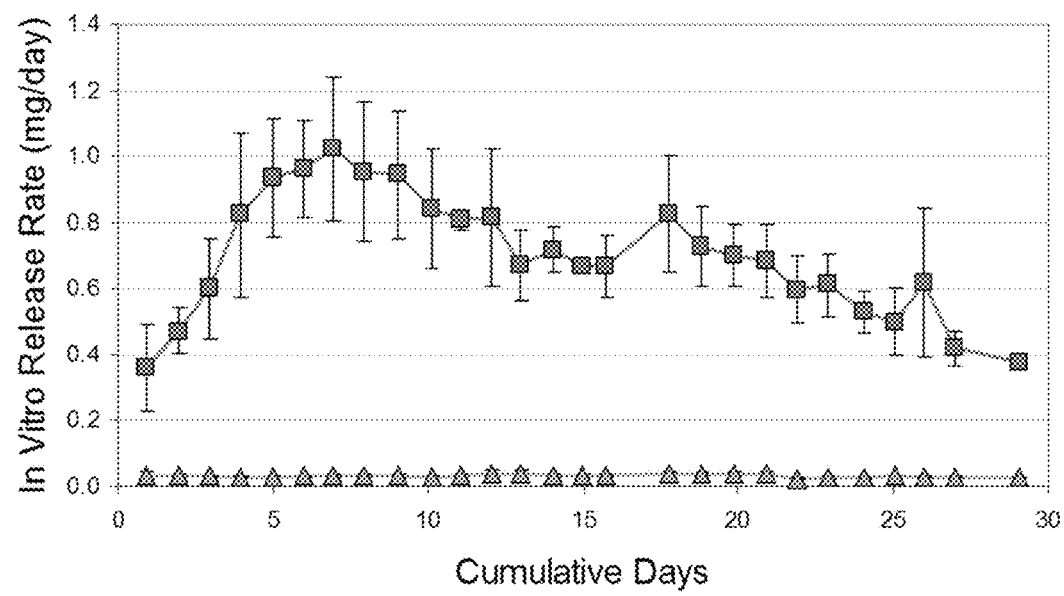
FIG. 12A is a graph showing the in vitro release rate, in mg/day, as a function of time, in days, for two groups (n=3) of delivery devices fitted at both ends with a porous partition and filled with an aqueous suspension of risperidone with a solubilizing excipient (squares) or without the excipient (triangles)

FIG. 12A shows in vitro release rates for the devices containing only risperidone (triangles) compared to devices containing risperidone plus PLGA (a mixture of PLGA 50:50 and PLGA 85:15, squares). The devices without PLGA shows limited release; devices with PLGA maintain a release rate above 0.4 mg/day for 30 days while those without PLGA release less than 0.05 mg/day throughout the same period.

Figure 12B:
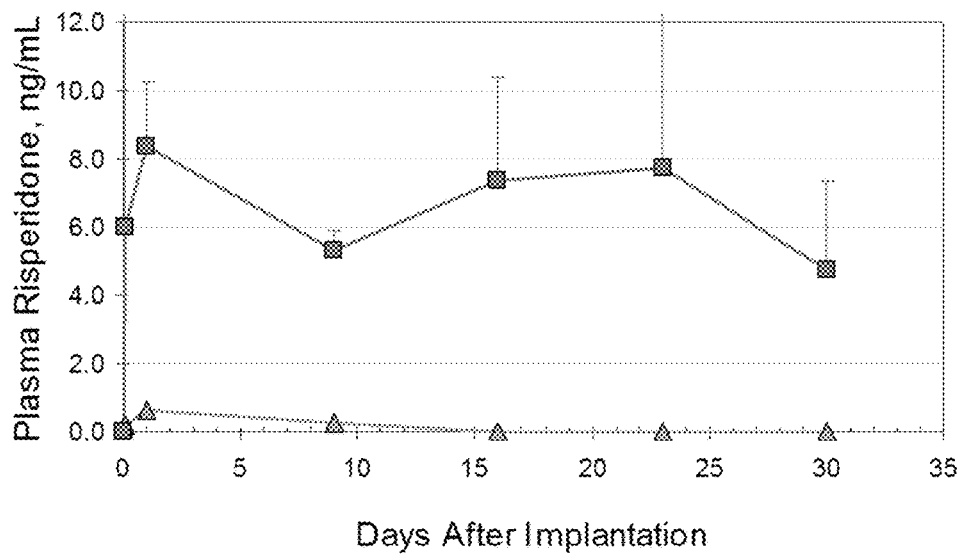
FIG. 12B is a graph showing the in vivo plasma concentration of risperidone and its active metabolite (9-hydroxy-risperidone), in ng/mL, as a function of time, in days, after subcutaneous implantation in rats of the devices of FIG. 12A, where the drug formulation comprised (squares) or lacked (triangles) a solubility-modifying agent.

FIG. 12B presents the comparable in vivo data. For the group containing risperidone only (triangles), plasma levels of risperidone (plus 9-hydroxyrisperidone) are barely detectable for the first week and then fall below the limits of quantitation of the assay (0.1 ng/mL). In the devices including a solubility-modifying agent (squares), plasma levels of risperidone (plus 9-hydroxyrisperidone) quickly build and maintain a level above 4 ng/mL for the entire one month period.

An excellent in vitro/in vivo correlation is apparent by comparing the data presented in FIGS. 12A-12B. It is apparent from this data that it is possible to optimize the in vivo performance of the devices using in vitro data. Increasing or prolonging output (or both) is possible by selection of the appropriate mass and erosion rates of the solubility-modifying agent(s).

Although the specific examples given herein are with respect to the model drug risperidone, it will be appreciated that any sparing soluble drug can be used in the device described herein. Example 6 illustrates devices designed for delivery of asenapine, a drug with a water solubility of 3 mg/mL at pH 7-7.4. The table below presents the solubility and pharmacokinetic parameters of exemplary drugs contemplated for use in the devices described herein.

| Parameter | Olanzapine | Paliperidone | Aripiprazole | Asenapine | Risperidone | Haloperidol |
|---|---|---|---|---|---|---|
| CL(L/hr) (iv) | 21 | | 2.37 | 52 | 2.84 | 42; 22 |
| CL (L/day) | 504 | | 57 | 1248 | 68 | 960 |

-continued

|  | Olanzapine | Paliperidone | Aripiprazole | Asenapine | Risperidone | Haloperidol |
|---|---|---|---|---|---|---|
| Target Steady state plasma conc (ng/mL) | 30 |  | 100 | 2.1 | 20 | 2 |
| Output rate | 15 |  | 5.7 | 2.62 | 1.36 | 1.92 |
| Half-life (hr) | 45 | 24 | 3 | 24 | 3 | 29 |
| Bioavailability |  |  |  |  |  |  |
| oral | 60% | 28% | 87% | 2% | 65 | 65% |
| sublingual |  |  |  | 30% |  |  |
| Water solubility (mg/mL) |  |  |  |  |  |  |
| neutral pH |  | 0.54 |  | 3.0 | 0.48 | 0.025 |
| acidic pH |  | 100 × neutral |  | 13 |  | 4.2 |

III. Methods of Treatment

In another aspect, methods for treating diseases or disorders using the device described herein above are provided. In particular embodiments, the implantable device delivers a therapeutic agent for between 1-3 months, more preferably for between 1-4 months, still more preferably for between 1-5 months, 1-6 months, 2-4 months, 2-6 months, or between 2-12 months. For chronic diseases, such as schizophrenia, bipolar disorder or alcoholism, patients may be treated from many months, perhaps years. In such disease settings, when one device is expended after several months of operation, it would be removed and replaced with a new, fully-charged device in order to provide uninterrupted therapy. The device can be implanted at the same, or a different site.

IV. Examples

The following examples are illustrative in nature and are in no way intended to be limiting.

Example 1

In Vitro Release of Risperidone

Typical Franz-type diffusion cells were fitted with porous partitions separating a donor chamber from a receptor chamber. The porous partitions were membranes with pore sizes of 3,000 Daltons molecular weight cut-off, 100,000 Daltons molecular weight cut-off and a 0.45 micron polyvinyldene-fluoride membrane filter (Durapore®). An aqueous suspension comprising risperidone (10 mg/mL PBS, pH 7.4) and poly(lactic-co-glycolic acid) was prepared and placed in the donor chamber of each cell. The cells were maintained at room temperature. Risperidone concentration in the buffer in the receptor chamber was measured by UV spectroscopy at 270 nm using an extinction coefficient for risperidone of 20.5. Buffer was diluted to 20-50 micrograms/mL prior to measurement to insure that the concentration was within the linear range of the UV measurement. Buffer was replaced each day. Results are shown in FIGS. 7A-7B.

Example 2

In Vitro Release of Risperidone

Franz diffusion cells were prepared as noted above. Aqueous suspensions comprising risperidone (10 mg) and 5 mg, 10 mg, or 15 mg of 85:15 poly(lactic-co-glycolic acid) were prepared and placed in the donor chamber of each cell. The cells were maintained at room temperature. Risperidone concentration in the buffer in the receptor chamber was measured by UV spectroscopy at 270 nm using an extinction coefficient for risperidone of 20.5. Buffer was diluted to 20-50 micrograms/mL prior to measurement to insure that the concentration was within the linear range of the UV measurement. Buffer was replaced each day. Results are shown in FIG. 8.

Example 3

In Vitro Release of Risperidone

Two groups of drug delivery devices were assembled as follows. Cylindrical titanium tubes, 4 mm in diameter and 35 mm in length, were prepared. Risperidone free base in the form of a dry powder (100 mg, Ren-Pharm Intl, particle size 2-100 micrometers) was filled into the a first group of devices (Group A, n=9). In a second group of devices (Group B, n=5), the same amount of risperidone was mixed with 5 mg 50:50 PLGA and with 15 mg 85:15 PLGA (Lakeshore Biomaterials, Birmingham, Ala.). The reservoirs of the devices were filled with phosphate buffered saline (PBS) at pH 7.4 under reduced pressure. Each of the devices in Group B was fitted with two regenerated cellulose membranes (5000 Daltons molecular weight cut off) at each end of the cylindrical tube by sandwiching the membrane between an o-ring and titanium frit (5 micron pores), as illustrated in FIGS. 5A-5B. The devices in Group A were identical, except the cellulose membrane was omitted, as illustrated in FIGS. 4A-4B. The devices were then placed individually in tubes containing approximately 1 mL PBS. The tubes were placed on a rotating rack (1 revolution per hour) at 37° C.

Figure 10:
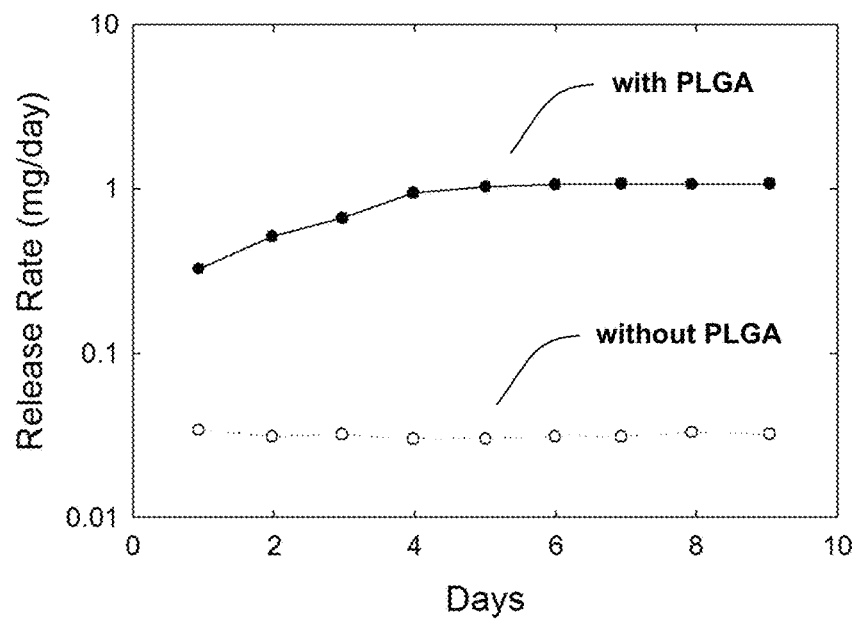
FIG. 10 is a graph of risperidone release rate, in mg/day, as a function of time, in days, for two devices in accord with the teachings herein, where one device included a mixture of two solubility-modifying agents (50:50 PLGA and 85:15 PLGA) in the drug suspension loaded into the device (closed circles) and the other device was filled with a drug suspension lacking a solubility-modifying agent (open circles)

Risperidone concentration in the recipient buffer was measured by UV spectroscopy at 270 nm using an extinction coefficient for risperidone of 20.5. Buffer was diluted to 20-50 micrograms/mL prior to measurement to insure that the concentration was within the linear range of the UV measurement. Buffer was replaced each day. The release rates for the devices in Group B (closed circles, with two different PLGAs) and Group A (open circles, without PLGA) are shown in FIG. 10. Devices without a solubility-modifying excipients released at a rate of less than 0.05 mg/day, far below the therapeutic dose level of >1 gm/day. In contrast, the devices with a solubility-modifying excipient, a mixture of two different PLGAs, released with an average of 1-1.2 mg/day, well within the target therapeutic range for risperidone.

Example 4

Devices with Mixture of PLGAs with Differential Aqueous Erosion Rates

The influence of lactic acid:glycolic acid ratio of PLGAs on the in vitro release rate of risperidone was investigated. Physical mixtures of 100 mg of risperidone and 5-15 mg of PLGA with lactic acid:glycoloic acid ratios of 50:50 and 85:15 were made and suspended in phosphate buffered saline. Risperidone release was measured as described in Example 1. Results are shown in FIG. 11. The first two curves in FIG. 11 show the release of risperidone mixed with two different samples of a 50:50 PLGA (DL1A and DL2A supplied by Lakeshore Biomaterials, Birmingham, Ala.). The third curve shows the release of risperidine when mixed with 15 mg of 85:15 PLGA (also obtained from Lakeshore Biomaterials, Birmingham, Ala.). The fourth and fifth curves illustrate the projected release of risperidone when mixed with PLGA with ratios of 90:10 and 95:5, respectively.

Example 5

In Vitro and In Vivo Delivery

Two groups of devices (n=6) were prepared. The main body of each device consisted of a cylindrical titanium tube, definining an internal reservoir. The tubes were 35 mm in length, with an outer diameter (OD) of 4.3 mm and an inner diameter (ID) of about 3 mm (Peridot Manufacturing, Pleasanton, Calif.). Both ends of each tube were tapered (lathed) so as to accept a press cap which served to retain a porous partition, as illustrated in FIGS. 4-5. The first group of devices was fitted on one end with a titanium sintered frit having a diameter 3.5 mm, a depth 0.5 mm, and a 5 micron nominal particle retention size (Applied Porous Materials, Farmington, Conn.). The frit was secured in each tube by placing the tube horizontally in a holder, and then positioning over the open end, in sequence, the frit, an o-ring and the press cap. The frit/o-ring stack was sealed in place on the edges of the reservoir by pressing downward the on the membrane press cup (Peridot Manufacturing, Pleasanton, Calif.) using a mechanical press (Schmidt Press No 307).

The devices were inverted and filled with 100 mg of dry powdered risperidone (Ren-Pharm Intl, particle size 2-100 micrometers). A 2.5 mm stainless steel ball was placed in the reservoir to provide mixing. A second frit was sealed to the remaining open end of the reservoir using the same procedure as described above for the other end.

The second group of devices were each fitted according to the same procedure, but include a circular 3.5 mm diameter polymer membrane (3KD MWCO Membranes, Millipore #PLBCO2510) positioned between the frit an o-ring as illustrated in FIGS. 5A-5B. The polymer membrane was intended to serve as a biocompatible interface between the frit and the subcutaneous tissue after implantation. The devices in the second group were filled with a physical mixture composed of 100 mg risperidone, 15 mg 50:50 PLGA and 50 mg 85:15 PLGA (Lakeshore Biomaterials, Birmingham, Ala.), plus the 2.5 mm stainless steel mixing ball.

After filling with drug and/or PLGA, all of the devices in each group were hydrated by placing each into a vacuum chamber, evacuating the chamber under vacuo, and back-filling with degassed PBS.

Both groups of devices were equally split, each subgroup of 3 devices destined for either in vitro or in vivo testing. In vitro release rate was determined by submerging the devices in 1 mL PBS held in screw cap cryo-vials. The tubes were sealed and placed in a rotating rack (1 revolution per hour) in a 37° C. incubator. Each day, each device was moved to a new tube containing fresh buffer, and the risperidone concentration in the release buffer was measured by UV spectroscopy.

For in vivo experiments, rats were anesthetized and devices placed subcutaneously in the dorsum, lateral to the midline, using a trocar. Whole blood samples were obtained by tail vein venous puncture. Plasma was immediately separated from formed elements by centrifugation. Plasma samples were sent to a reference laboratory (Integrated Analytics Solutions, Berkeley, Calif.) for detection of risperidone and 9-hydroxyrisperidone concentrations in the plasma, and were quantified by a validated LC/MS/MS method. The lower limit of quantitation was 0.10 ng/mL. Results are shown in FIGS. 12A-12B.

FIG. 12A shows in vitro release rates for the devices containing only risperidone compared to devices containing risperidone plus PLGA (a mixture of PLGA 50:50 and PLGA 85:15 as described above). The group without PLGA shows limited release; devices with PLGA maintain a release rate above 0.4 mg/day for 30 days while those without PLGA release less than 0.05 mg/day throughout the same period.

FIG. 12B presents the comparable in vivo data. For the group containing risperidone only, plasma levels of risperidone (plus 9-hydroxyrisperidone) are barely detectable for the first week and then fall below the limits of quantitation of the assay (0.1 ng/mL). In the group with PLGA, on the other hand, plasma levels of risperidone (plus 9-hydroxyrisperidone) quickly build and maintain a level above 4 ng/mL for the entire one month period. An excellent in vitro/in vivo correlation is apparent by comparing the data presented in FIGS. 12A and 12B.

Example 6

Device for Delivery of Asenapine

Asenapine exemplifies an agent that will benefit from the device described herein. This agent has recognized activity in the treatment of schizophrenia and bipolar disorder but suffers from a number of factors that detract from its clinical benefit. It has poor oral bioavailability (<2%) due to a high first pass effect; its current dosage form is a sublingual tablet that must be taken twice daily, making compliance in the target patient population challenging. Asenapine is cleared rapidly from circulation (plasma clearance 52 L/hr) but is active at low plasma concentrations (70% $D_2$ receptor occupancy at 2.1 ng/mL). For the drug delivery device enabled herein, the required output rate can be calculated by multiplying the CL (in mL/day) times the steady state plasma concentration required for efficacy (mg/mL): =$1.25 \times 10^6$ mL/day×$2.1 \times 10^{-6}$ mg/mL=2.65 mg/day output to maintain 2.1 ng/mL.

The drug exhibits limited water solubility at neutral pH (3 mg/mL at pH 7.0) but its solubility improves as the pH is lowered (13 mg/mL in 0.1N HCl).

The drug delivery device claimed herein typically would consist of a titanium cylinder of 3.8 mm ID and 40 mm in length fitted at each end with sintered titanium frits of 0.2 cm in thickness and a pore size of ≤2 μm. The volume of the reservoir=$\pi r^2 h$=453 The combined surface area of the two frits is 0.23 cm$^2$; the porosity of the frits is 30%, so the effective pore area available for diffusion is 0.07 cm$^2$. If the reservoir were filled with an aqueous suspension of 250 mg of just the drug, the flux (the outward diffusion) at neutral pH can be calculated from Fick's law: J(mg/sec)=D(cm/sec)×ΔC(the concentration gradient between the inside and outside of the reservoir expressed as mg/cm$^3$)/0.2 cm (the thickness of the diffusion membrane, or frit thickness in this case)×A (effective pore area available for diffusion expressed as cm$^2$). The concentration in the external medium (intersitial fluid) can be considered to be zero. The concentration within the aqueous phase of the reservoir will be 3 mg/mL, the drug's inherent solubility at neutral pH, so ΔC=3 mg/mL, or 3 mg/cm$^3$. The diffusion coefficient of the drug can be approximated to be that of a small molecule such as glucose ($7\times10^{-6}$ cm$^2$/sec). Thus at neutral pH, flux would be $7\times10^{-6}$ cm·sec$^{-1}\times3$ mg·cm$^{3-1}$/0.2 cm×0.07 cm$^2$=7.35×10$^{-6}$ mg·sec$^{-1}$. Converting J to mg/day, the maximum flux under these conditions would be 0.6 mg/day. This level falls short of the output needed to provide a therapeutic dose of the drug, 2.65 mg/day, by fourfold.

The current device provides a means to boost the output rate of asenapine by loading a mixture of PLGA polymers together with the drug. In this case 250 mg of drug plus approximately 200 mg of PLGA would be loaded into the 450 μL reservoir. The device is hydrated and implanted under the skin. As the PLGA hydrolyses over time, lactic acid and glycolic acid equivalents are generated from the insoluble polymer within the reservoir, effectively lowering the internal pH. Furthermore, the lactide and glycolide monomers form a salt with the asenapine base and improve the drug's water solubility within the reservoir to at least 13 mg/mL. Recalculating flux under these conditions the output rate would be 2.6 mg/day, and, given the total drug loaded is 250 mg, this output can be maintained for 96 days, thus providing a therapeutic level of drug for a 3-month period following implantation.

Comparative Example 1

Prior art devices as described in U.S. Pat. Nos. 3,896,819; 3,948,254; 3,948,262; 3,993,072; and 3,993,073 were examined and compared to the present device. The deficiency of the prior art devices is apparent by examining the in vivo data presented in FIG. 12B, wherein two devices are compared; one modeled after the teachings of these prior art documents and the other after the present teachings. In this comparison, devices are cylindrical reservoirs, the outer surface of which is a smooth biocompatible, satin-finished surface, suitable for implantation under the skin. The ends of the reservoir are fitted with porous partitions. The bioavailability data for such devices containing only risperidone (lower curve, triangles) and modeled after the prior art teaching (i.e., "surrounded by an enclosure that at least is partially formed by a microporous membrane designed to be permeable to the drug") do not provide output sufficient to maintain a therapeutic dose. This is because the aqueous solubility of risperidone is too low to create a concentration gradient sufficient to drive mass transport of the drug across the porous surface of devices with this configuration. In contrast, devices containing a preferred solubility-modifying excipient as described herein produce a therapeutic level active drug for at least one month (upper curve, squares).

The limitations of the prior art device, in the case of risperidone, are illustrated in the following analysis. The aqueous solubility of risperidone at pH 7.4 is about 0.42 mg/mL. Thus, when the carrier fluid is water and an aqueous suspension of risperidone is loaded into the device contemplated in the prior art device, and applying Fick's law, the porous surface area required to produce an output rate of about 1.78 mg/day (i.e., the dose required to maintain a therapeutic response of this drug) can be calculated.

The assumptions for this illustration are:
i. The equilibrium solubility of risperidone free base in PBS is 0.42 mg/mL at pH 7.4.
ii. The external concentration will effectively be zero, so the concentration gradient is approximated by the internal concentration (i.e., 0.42 mg/mL).
iii. The output rate (release rate) desired for the product, based on the dose rate of Risperdal Consta, is 1.78 mg/day (i.e., based on the recommended dose of Risperdal Consta of 25 mg dose every 2 weeks, www.risperdalconsta.com).
iv. The diffusion constant of risperidone is equal to that of glucose ($7\times10^{-6}$ cm$^2$/sec, http://www.d.umn.edu/~dlong/samrpt.html).
v. The thickness of porous portion of the encasement is $1.2\times10^{-1}$ cm.
vi. The porosity of the porous portion of the encasement is 50%.

If the OD of the porous encasement is 4.6 mm and the ID is 2.2 mm, the surface area of the inner exposure of the porous segment needed to provide the desired release rate is calculated as follows. First, the release rate, is restated in terms of mg per sec:

$$\text{Release Rate}(R) = \frac{1.78 \text{ mg}}{\text{day}} = \frac{1.78 \text{ mg}}{8.64 \times 10^4 \text{sec}} = 2.05 \times 10^{-5} \text{mg} \cdot \text{sec}^{-1} \quad (8)$$

Flux is expressed in terms of the number of molecules (or mass) which diffuse through a defined area per unit time. In this case flux has the units mg·sec$^{-1}$·cm$^{3-1}$, accounting for the movement of molecules through a defined surface area of the membrane (which shall be called "A"). It is this area that we wish to determine.

Fick's law states (units in parentheses):

$$J(\text{mg} \cdot \text{cm}^{2-1} \cdot \text{sec}^{-1}) = D(\text{cm}^2 \cdot \text{sec}^{-1}) \cdot \frac{C(\text{mg} \cdot \text{cm}^{3-1})}{T(\text{cm})} \quad (9)$$

Expressing flux in terms of release rate ("R"), it's necessary to include the surface area available for diffusion, that is: R÷membrane surface area (A):

$$C(\text{mg} \cdot \text{cm}^{3-1}) = \frac{\frac{R(\text{mg} \cdot \text{sec}^{-1})}{A(\text{cm}^2)} \cdot T(\text{cm})}{D(\text{cm}^2 \cdot \text{sec}^{-1})} \quad (10)$$

Wherein D is the diffusion constant of the agent; and $T_M$=the thickness of the porous section. Inserting the values for concentration, release rate and thickness:

$$0.4 \text{ mg} \cdot \text{cm}^{-3} = \frac{\frac{2.05 \times 10^{-5} \text{mg} \cdot \text{sec}^{-1}}{A} \times 1.2 \times 10^{-1} \text{cm}}{7 \times 10^{-6} \cdot \text{cm}^2 \cdot \text{sec}^{-1}} \quad (11)$$

Rearranging and solving for A:

$$A = \frac{2.47 \times 10^{-6} \text{mg} \cdot \text{cm} \cdot \text{sec}^{-1}}{(7 \times 10^{-6} \cdot \text{cm}^2 \cdot \text{sec}^{-1}) \cdot (0.42 \text{ mg} \cdot \text{cm}^{3-1})} \quad (12)$$

$$A = 0.84 \text{ cm}^2$$

In practice, only up to about 50% of this area is available for diffusion, so the effective porous surface area ($A_{Eff}$) needed is:

$$A_{Eff} = \frac{0.84 \text{ cm}^2}{.50} = 1.68 \text{ cm}^2 \quad (13)$$

Thus, in the case of risperidone, owing to its low aqueous solubility, a device modeled after the prior art device teachings would require at least 1.7 cm² of porous surface area in order to provide a therapeutic dose in vivo.

For the reasons detailed above, the device as described herein, which is designed to be implanted subcutaneously, is cylindrical with smooth walls. The porous partition needed for drug diffusion is fitted on one or both ends of the cylindrical reservoir. A typical device would have an OD of 0.46 cm so that the device can be comfortably placed under the skin. Given the thickness of the wall required for mechanical strength, the ID of the reservoir is 0.22 cm. So the maximum porous surface area available for a device with smooth tubular surfaces and fitted at both ends with a circular porous partition is:

$$A = \pi r^2 = \pi(0.11)^2 = 0.04 \text{ cm}^2 \quad (14)$$

and for two membranes $$0.04 \text{ cm}^2 \times 2 = 0.08 \text{ cm}^2 \quad (15)$$

A device of this size and shape, which is suitable for subcutaneous implantation, using an aqueous carrier fluid and modeled on the teachings of the prior art device, would not provide sufficient drug output when risperidone or other agents with similarly low aqueous solubility are selected. As shown in the calculations above, following the teachings of the prior art device, an effective porous surface area of at least 1.7 cm² would be needed to provide a therapeutic dose of risperidone (Equation 13). However, in the configuration described herein which is suitable for subcutaneous implantation, the porous partition provides only a 0.08 cm² of effective surface area, 20 times below the value needed by the prior art device.

As described below, and presented graphically in FIG. 12A-12B, the current device overcomes the limitations of both the prior art devices and achieves a sufficient output rate of risperidone and other drugs with similarly low aqueous solubility properties.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

It is claimed:

1. A method for delivering a sparingly water soluble drug into an environment of use, comprising:
providing a device comprising a porous partition with pores having a pore size and with a porosity, a reservoir and a formulation contained in the reservoir, the formulation comprising a sparingly water soluble drug having a soluble form and an insoluble form and a solubility-modifying excipient that generates acidic groups for a period of between about 2-12 months to provide, when the formulation is hydrated, a concentration of drug in the soluble form that is released across the porous partition and a concentration of drug in the insoluble form that is retained by the porous partition, and
delivering a therapeutic dose of the drug for the period, wherein delivering the therapeutic dose is dependent on pH of the drug formulation and independent of pore size of the porous partition with said porosity.

2. The method according to claim 1, wherein the excipient is a biocompatible, bioerodible polymer.

3. The method according to claim 2, wherein the polymer is selected from the group of polylactides, polyglycolides, copolymers thereof, and polyethyleneglycol.

4. The method according to claim 2, wherein the polymer is a co-polymer of polylactic acid and polyglycolic acid monomeric units, wherein the polylactic acid content is between about 50% to 100%.

5. The method according to claim 1, wherein the solubility-modifying excipient is an erodible polymer or a degradable polymer.

6. The method according to claim 5, wherein the polymer is polymerized from a monomer selected from the group consisting of lactic acid, glycolic acid, lactide, glycolide, ethylene oxide and ethylene glycol.

7. The method according to claim 5, wherein the polymer is a poly(lactic-co-glycolic acid) copolymer.

8. The method according to claim 1, wherein the solubility-modifying excipient is water insoluble.

9. The method according to claim 8, wherein the solubility-modifying excipient is retained by the porous partition.

10. The method according to claim 1, wherein the solubility-modifying excipient is a water insoluble polymer.

11. The method according to claim 10, wherein the solubility-modifying excipient undergoes hydrolysis to form a water-soluble monomer.

12. The method according to claim 1, wherein said drug is a neuroleptic agent.

13. The method according to claim 12, wherein the neuroleptic agent is risperidone, 9-hydroxyrisperidone, olanzapine, or a pharmaceutically acceptable salt thereof.

14. The method according to claim 1, wherein said drug is risperidone.

15. The method according to claim 1, wherein the drug is selected from the group consisting of buprenorphine, paliperidone, asenapine, haloperidol, aripiprazole, and pharmaceutically acceptable salts thereof.

16. A method for treating a patient with a sparingly water soluble drug, comprising:
implanting a device comprising a porous partition with pores having a pore size and with a porosity, a reservoir and a formulation contained in the reservoir, the formulation comprising a sparingly water soluble drug having a soluble form and an insoluble form and a solubility-modifying excipient that generates acidic groups for a period of between about 2-12 months to provide, when the formulation is hydrated to form an aqueous suspension, a concentration of drug in the soluble form that is released across the porous partition and a concentration of drug in the insoluble form that is retained by the porous partition, and delivering a therapeutic dose of the drug for the period, wherein delivering the therapeutic dose is dependent on pH of the drug formulation and independent of pore size of the porous partition with said porosity.

17. The method according to claim 16, wherein the device is implanted subcutaneously.

* * * * *

UNITED STATES PATENT AND TRADEMARK OFFICE
CERTIFICATE OF CORRECTION

PATENT NO. : 10,391,288 B2
APPLICATION NO. : 15/388298
DATED : August 27, 2019
INVENTOR(S) : Martin et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 412 days.

Signed and Sealed this
Nineteenth Day of May, 2020

Andrei Iancu
*Director of the United States Patent and Trademark Office*